(12) United States Patent
Rutherford et al.

(10) Patent No.: US 10,791,104 B2
(45) Date of Patent: Sep. 29, 2020

(54) SYSTEMS AND METHODS FOR AUTHENTICATING USERS OF A COMPUTER SYSTEM

(71) Applicant: ASIGNIO, INC., Sedro Woolley, WA (US)

(72) Inventors: Kyle Rutherford, Sedro Woolley, WA (US); Eric Dustrude, Bellingham, WA (US); Erik Hodge, Anderson Island, WA (US); Benjamin MacKay, Burlington, WA (US); Calvin Rutherford, Sedro Woolley, WA (US); Kevin Boyd, New Providence, NJ (US)

(73) Assignee: ASIGNIO INC., Sedro Woolley, WA (US)

( * ) Notice: Subject to any disclaimer, the term of this patent is extended or adjusted under 35 U.S.C. 154(b) by 0 days.

(21) Appl. No.: 15/358,052

(22) Filed: Nov. 21, 2016

(65) Prior Publication Data
US 2017/0149757 A1     May 25, 2017

Related U.S. Application Data

(60) Provisional application No. 62/258,006, filed on Nov. 20, 2015.

(51) Int. Cl.
*H04L 29/06*     (2006.01)
*H04W 12/06*     (2009.01)
(Continued)

(52) U.S. Cl.
CPC .......... *H04L 63/08* (2013.01); *G06F 19/3456* (2013.01); *G06F 21/31* (2013.01);
(Continued)

(58) Field of Classification Search
CPC .......... G06F 21/36; G06F 21/32; G06F 21/31; H04L 63/18; H04L 2463/082
See application file for complete search history.

(56) References Cited

U.S. PATENT DOCUMENTS

| | | | |
|---|---|---|---|
| 5,347,589 A | 9/1994 | Meeks et al. | |
| 8,256,664 B1 * | 9/2012 | Balfanz | G06F 21/43 235/375 |

(Continued)

FOREIGN PATENT DOCUMENTS

| | | |
|---|---|---|
| WO | 2008043090 A1 | 4/2008 |
| WO | 2017087981 A2 | 5/2017 |

(Continued)

OTHER PUBLICATIONS

USPTO, "Final Office Action, U.S. Appl. No. 14/501,554", dated Jun. 21, 2017, 16 pages.
(Continued)

*Primary Examiner* — James R Turchen
(74) *Attorney, Agent, or Firm* — Michael R. Schacht; Schacht Law Office, Inc.

(57) ABSTRACT

An authentication system for allowing access to a user account server has at least one access device and at least one verification server. The at least one access device is capable of operatively connecting to the user account server and comprises a touch screen for allowing entry of session signatures. The at least one verification server is capable of comparing session signatures to reference signatures. A user reference signature is stored on the at least one verification server. The at least one access device allows entry of a user session signature and transmission of the user session signature to the at least one verification server. The at least one verification server allows the at least one user to connect to (Continued)

the user account server based on a comparison of the user session signature with the user reference signature.

20 Claims, 24 Drawing Sheets

(51) Int. Cl.
*G06F 21/36* (2013.01)
*G06F 21/32* (2013.01)
*G06F 21/31* (2013.01)
*G06F 19/00* (2018.01)
*G06K 7/14* (2006.01)
*G06Q 40/02* (2012.01)
*G06K 9/00* (2006.01)
*H04W 12/00* (2009.01)

(52) U.S. Cl.
CPC .............. *G06F 21/32* (2013.01); *G06F 21/36* (2013.01); *G06K 7/1417* (2013.01); *G06Q 40/025* (2013.01); *H04L 63/10* (2013.01); *H04L 63/102* (2013.01); *H04L 63/18* (2013.01); *H04W 12/06* (2013.01); *G06K 9/00154* (2013.01); *H04L 2463/082* (2013.01); *H04W 12/00522* (2019.01)

(56) References Cited

U.S. PATENT DOCUMENTS

| | | | |
|---|---|---|---|
| 8,601,560 | B2 | 12/2013 | Kim et al. |
| 9,020,525 | B2 | 4/2015 | Murphy et al. |
| 9,338,164 | B1* | 5/2016 | Liu .................... H04L 63/0869 |
| 9,374,369 | B2 | 6/2016 | Mahaffey et al. |
| 9,641,520 | B2* | 5/2017 | Neuman .................... H04L 9/30 |
| 9,686,272 | B2 | 6/2017 | Blinn |
| 9,805,182 | B1* | 10/2017 | Kayyidavazhiyil ..... G06F 21/36 |
| 9,813,411 | B2* | 11/2017 | Thibadeau, Sr. ... H04L 63/0807 |
| 9,836,741 | B2* | 12/2017 | Varadarajan ....... G06Q 20/3276 |
| 9,866,549 | B2* | 1/2018 | Thibadeau, Sr. ....... G06F 21/36 |
| 9,887,999 | B2* | 2/2018 | Dong ................. H04L 63/0884 |
| 10,083,436 | B1 | 9/2018 | Rutherford et al. |
| 2003/0182585 | A1* | 9/2003 | Murase ................... G06F 21/32 726/3 |
| 2003/0233557 | A1 | 12/2003 | Zimmerman |
| 2005/0091500 | A1* | 4/2005 | Okazaki ............. G06K 9/00154 713/176 |
| 2007/0188793 | A1* | 8/2007 | Wakai ................ G06K 9/00161 358/1.14 |
| 2008/0020733 | A1* | 1/2008 | Wassingbo .............. G06F 21/32 455/411 |
| 2008/0049986 | A1* | 2/2008 | Arai ................... G06K 9/00187 382/119 |
| 2009/0210939 | A1* | 8/2009 | Xu ..................... G06K 9/00154 726/19 |
| 2009/0320123 | A1* | 12/2009 | Yu ..................... H04W 12/0605 726/16 |
| 2010/0008551 | A9 | 1/2010 | Schiller et al. |
| 2010/0139992 | A1* | 6/2010 | Delia ....................... G06F 21/32 178/19.01 |
| 2011/0047608 | A1 | 2/2011 | Levenberg |
| 2011/0156867 | A1* | 6/2011 | Carrizo .................... G07C 9/35 340/5.85 |
| 2011/0270751 | A1* | 11/2011 | Csinger .................. H04L 63/18 705/42 |
| 2011/0302649 | A1* | 12/2011 | Foster ..................... G06F 21/36 726/19 |
| 2012/0102551 | A1 | 4/2012 | Bidare |
| 2012/0317628 | A1* | 12/2012 | Yeager ................. G06Q 20/204 726/5 |
| 2012/0330769 | A1 | 12/2012 | Arceo |
| 2013/0111580 | A1* | 5/2013 | Checco .................... G06F 21/32 726/19 |
| 2013/0145446 | A1* | 6/2013 | Dorso ..................... G06F 21/36 726/6 |
| 2013/0148024 | A1 | 6/2013 | Shin et al. |
| 2014/0007205 | A1* | 1/2014 | Oikonomou ........ H04L 63/0853 726/6 |
| 2014/0173287 | A1* | 6/2014 | Mizunuma .......... H04L 63/0407 713/176 |
| 2014/0282961 | A1* | 9/2014 | Dorfman ................. G06F 21/35 726/7 |
| 2014/0297433 | A1* | 10/2014 | Bielamowicz ........ G06F 21/316 705/18 |
| 2014/0375573 | A1 | 12/2014 | Idzik et al. |
| 2015/0046276 | A1 | 2/2015 | Artman et al. |
| 2015/0071505 | A1 | 3/2015 | Kim et al. |
| 2015/0237031 | A1* | 8/2015 | Neuman .................. H04L 63/08 713/176 |
| 2015/0312252 | A1* | 10/2015 | Potonniee ............. H04L 63/083 726/7 |
| 2015/0334108 | A1* | 11/2015 | Khalil .................... H04W 12/06 726/8 |
| 2015/0347734 | A1* | 12/2015 | Beigi .................... H04L 9/3263 713/155 |
| 2016/0057135 | A1* | 2/2016 | Jiang ........................ H04L 63/08 713/172 |
| 2016/0132673 | A1* | 5/2016 | Birk ........................ G06F 21/30 726/19 |
| 2016/0191506 | A1* | 6/2016 | Wang ..................... H04L 63/18 726/7 |
| 2016/0259895 | A1* | 9/2016 | Austermann ........... H04L 51/32 |
| 2016/0314462 | A1* | 10/2016 | Hong ................. G06Q 20/3274 |
| 2016/0337351 | A1* | 11/2016 | Spencer ............. H04L 63/0876 |
| 2017/0060812 | A1* | 3/2017 | Williams .............. G06F 40/106 |
| 2018/0205716 | A1 | 7/2018 | Rutherford et al. |
| 2019/0066092 | A1 | 2/2019 | Rutherford et al. |

FOREIGN PATENT DOCUMENTS

| | | |
|---|---|---|
| WO | 2017087981 A3 | 8/2017 |
| WO | 2018132844 A1 | 7/2018 |

OTHER PUBLICATIONS

International Searching Authority, ISR & Written Opinion, PCT/US2016/063196, dated May 18, 2017, 7 pages.
Zoltan Puskas, Some Stuff, Android Unlock Pattern Security Analysis, https://sinustrom.info/2012/05/21/android-unlock-pattern-security-analysis/, May 21, 2012, 3 pages.
USPTO, "Non-Final Office Action, U.S. Appl. No. 14/501,554," dated Jan. 16, 2018, 12 pages.
International Searching Authority, ISR & Written Opinion, PCT/US18/13916, dated Jun. 21, 2018, 8 pages.
International Searching Authority, ISR & Written Opinion, PCT/US2018/056936, dated Jan. 31, 2019, 8 pages.

* cited by examiner

SYSTEMS AND METHODS FOR AUTHENTICATING USERS OF A COMPUTER SYSTEM

RELATED APPLICATIONS

This application, U.S. patent application Ser. No. 15/358,052 filed Nov. 21, 2016, claims benefit of U.S. Provisional Application Ser. No. 62/258,006 filed Nov. 20, 2015, the contents of which are incorporated herein by reference.

TECHNICAL FIELD

The present invention relates to systems and methods for authenticating users of a website and, more specifically, to such systems and methods that increase security while maintaining usability.

BACKGROUND

Websites often maintain specific information for a particular user in a user account specific to that particular user. Because a user account may contain sensitive information, websites that maintain user accounts are typically configured to request the verification that a user attempting to obtain access to a particular user account is the particular user associated with that particular user account. Perhaps the most common method of verifying that access to a particular user account is restricted to the particular user associated with that account is to require the entry of a user name and password created by the particular user. For a variety of reasons, user names and passwords are conventionally considered not to an ideal method of restricting access to a user account.

The need thus exists for systems and methods of restricting access to user accounts in addition to or instead of the entry of a user name and password.

SUMMARY

The present invention may be embodied as an authentication system for allowing access to a user account server comprising at least one access device and at least one verification server. The at least one access device is capable of operatively connecting to the user account server, where the at least one access device comprises a touch screen for allowing entry of session signatures. The at least one verification server capable of comparing session signatures to reference signatures. The at least one user establishes a user reference signature that is stored on the at least one verification server. The at least one user operates the at least one access device to enter a user session signature. The at least one access device transmits the user session signature to the at least one verification server. The at least one verification server allows the at least one user to connect to the user account server based on a comparison of the user session signature with the user reference signature.

The present invention may also be embodied as a method of allowing access to a user account server comprising the following steps. At least one access device is operatively connected to the user account server, where the at least one access device comprises a touch screen for allowing entry of session signatures. At least one verification server capable of comparing session signatures to reference signatures is provided. A user reference signature is stored on the at least one verification server. The at least one access device is operated to enter a user session signature. The at least one access device is operated to transmit the user session signature to the at least one verification server. The at least one verification server is operated to allow the at least one user to connect to the user account server based on a comparison of the user session signature with the user reference signature.

The present invention may also be embodied as an authentication system for allowing access to a controlled data stored on a user account server comprising at least one access device and at least one verification server. The at least one access device is capable of operatively connecting to the user account server, where the at least one access device comprises a touch screen for allowing entry of session signatures. The at least one verification server is capable of comparing session signatures to reference signatures. The at least one user establishes a user reference signature that is stored on the at least one verification server. The at least one user operates the at least one access device to enter a user session signature. The at least one access device transmits the user session signature to the at least one verification server. The at least one verification server allows the at least one user to access the controlled data on the user account server based on a comparison of the user session signature with the user reference signature.

DETAILED DESCRIPTION

Figure 1:
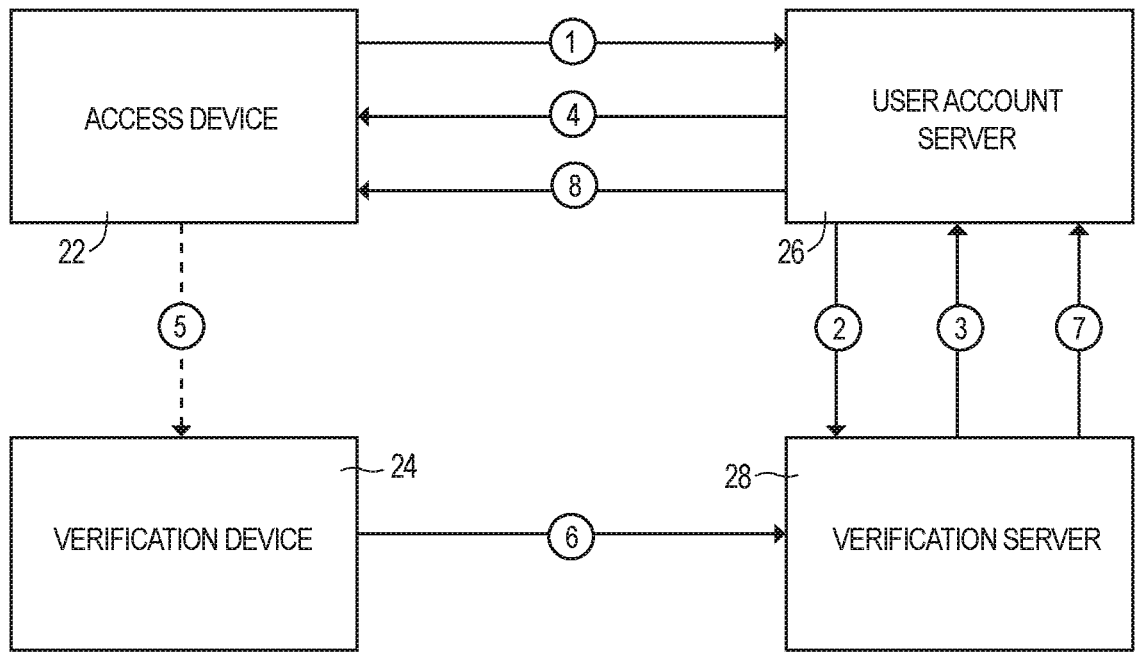
FIG. 1 is a generic block diagram of a verification system constructed in accordance with, and embodying, the principles of the present invention.

The present invention may be embodied in a number of different forms, and several examples of authentication systems and methods constructed in accordance with the principles of the present invention will be described in detail below.

I. Website Log-In Example

The present invention may be embodied as a verification system 20 that provides the ability to login and/or authenticate for an app or website using a host device. The example verification system 20 comprises at least one primary access device 22, at least one verification access device 24, a remote user account server 26 associated with the user account to be accessed, and a verification server 28. In this example, the primary access device 22 is a desktop computer without a touch screen. The example user account server 26 is a combination of computer hardware and software forming an online service such as a shopping website, bank website, government website, or other service defining user accounts and containing data the access to which is controlled (e.g., controlled data). The example verification access device 22 is a computing device having a touch screen. The example verification server 28 is a combination of computer hardware and software forming an online service capable of storing data and performing a compare operation as will be described below.

While the verification access device 24 and verification server 28 are depicted separately in FIG. 1, these services may be performed on a single piece of hardware. For example, the verification access device 24 may contain software forming the verification server 28. As another alternative, more than one verification server 28 may be provided.

The website log-in verification process works generally as follows.

Figure 2:
FIG. 2 is a screen shot of a display generated by an access device in a pre-log-in mode of a generic example of the present invention.
Figure 3:
FIG. 3 is a screen shot of a display generated by the access device in a log-in mode in the generic example.

1. A web page served by a client maintaining a client user account server is opened using the primary access device 22. The web page includes a verification server plug-in control. As shown in FIG. 2, the verification server plug-in control displays one or more buttons 30 in a display area on the primary access device 22. When the button 30 is clicked, a process associated with either screen element calls the verification server 28 if the verification server 28 is installed on the primary access device 22. The screen element process requests a unique login code image 32 from the verification server 28 and displays this as a code image such as a QR code on the web page as shown in FIG. 3. The code image 32 may be any graphic element recognizable using image analysis software. While such image analysis software is widely available for recognizing QR codes, other images may be used to establish a link between the primary access device 22 and the verification access device 24. For example, a photograph and facial recognition software may be used to establish this link. A pattern and pattern matching software may also be used.

2. Accordingly, after the appropriate button is activated by, for example, touching or clicking, a code image 32 such as a QR code is thus displayed on the web page as shown in FIG. 3. The code image is associated with a session ID. Typically, the session ID is associated with a time period during which the authentication process must be completed.

Figure 4:
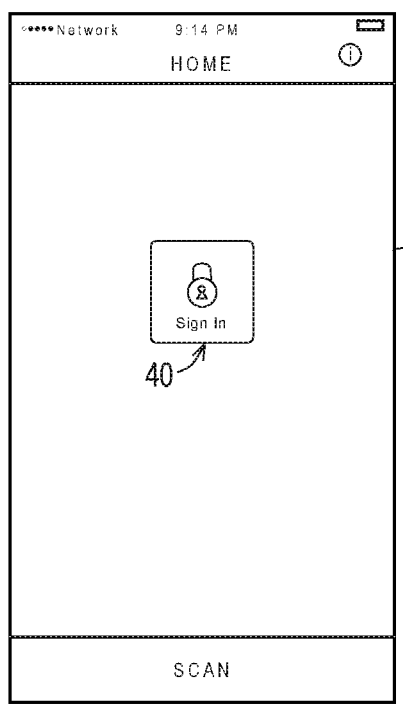
FIG. 4 is a screen shot of a display generated by a verification device in a pre-scan mode in the generic example.
Figure 5:
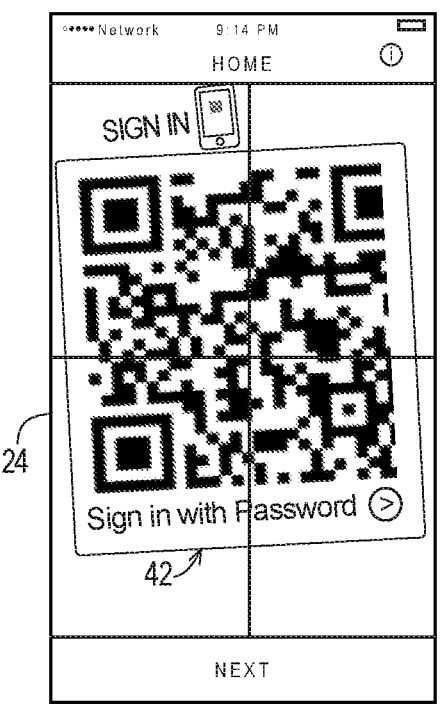
FIG. 5 is a screen shot of a display generated by the verification device in a scan mode in the generic example.
Figure 6:
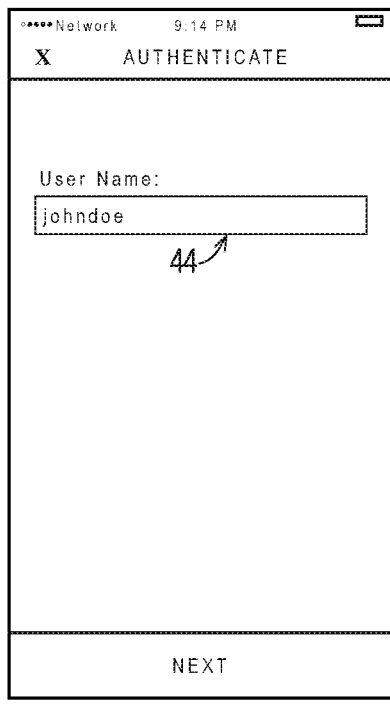
FIG. 6 is a screen shot of a display generated by the verification device in a pre-authentication mode in the generic example.

3. The user's mobile verification access device 24, running verification device software, is used to scan the code image 32 as shown in FIGS. 4 and 5. A scan button 40 is touched, and a scan 42 of the code image 4322 is displayed on the verification access device 24 while the code contained in the code image 32 is verified by the verification server 28. After the code image 32 has been scanned, the user's name is confirmed in a text box 44 as shown in FIG. 6.

Figure 7:
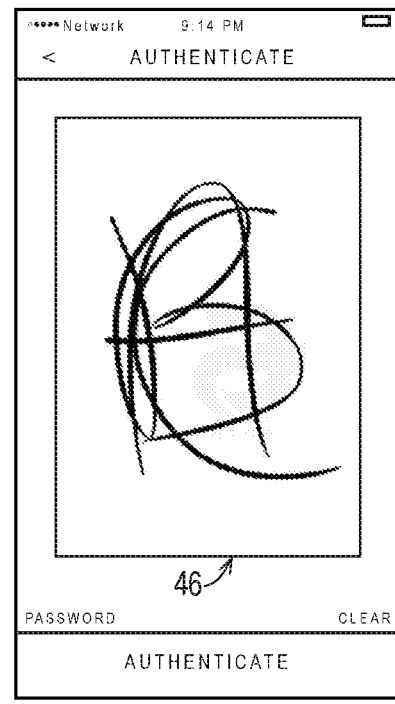
FIG. 7 is a screen shot of a display generated by the verification device in an authentication mode in the generic example.

4. The user next authenticates by "signing" on the mobile verification access device 24 as shown at 46 in FIG. 7. The mobile verification access device 24 and/or verification server 28 perform calculations to match a user session signature against stored "master" or user reference signature, thereby verifying the identity of the user.

5. If user's session signature passes, the verification server 28 returns a login token to the web page on the primary access device 22 and to the client user account server 26.

6. The verification server 28 passes token back up to client user account server 26.

7. The client user account server 26 calls the verification server 28 with a login token to get login credentials.

8. The verification server 28 returns login credentials to the user account server 26.

Figure 8:
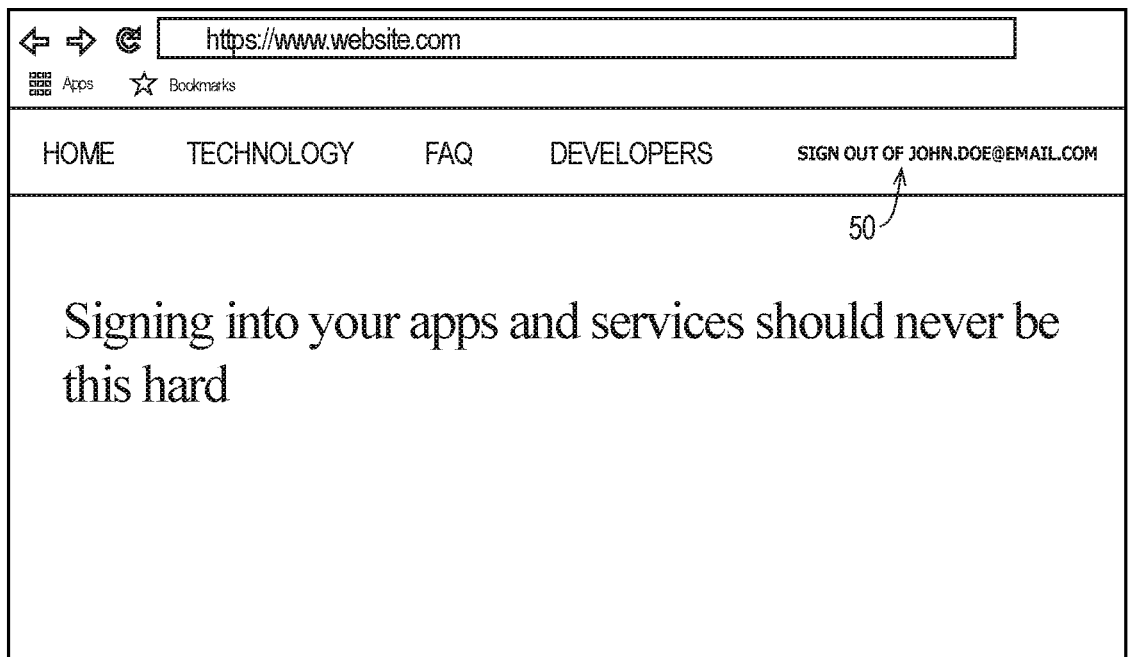
FIG. 8 is a screen shot of a display generated by the access device in a signed in or logged in mode in the generic example.

9. The client user account server 26 validates the user, and the user is logged in to the web page displayed on the primary access device 22 as shown at 50 in FIG. 8.

In the context of logging into an online service formed by the remote user account server 26, the login process may be performed after visiting the site. For example, for online shopping, the user may be encouraged to shop and fill an online shopping cart and log in only at check out. However, in the case of online banking, the user will likely be required to log in before accessing any confidential information.

II. Financing Example

Figure 9:
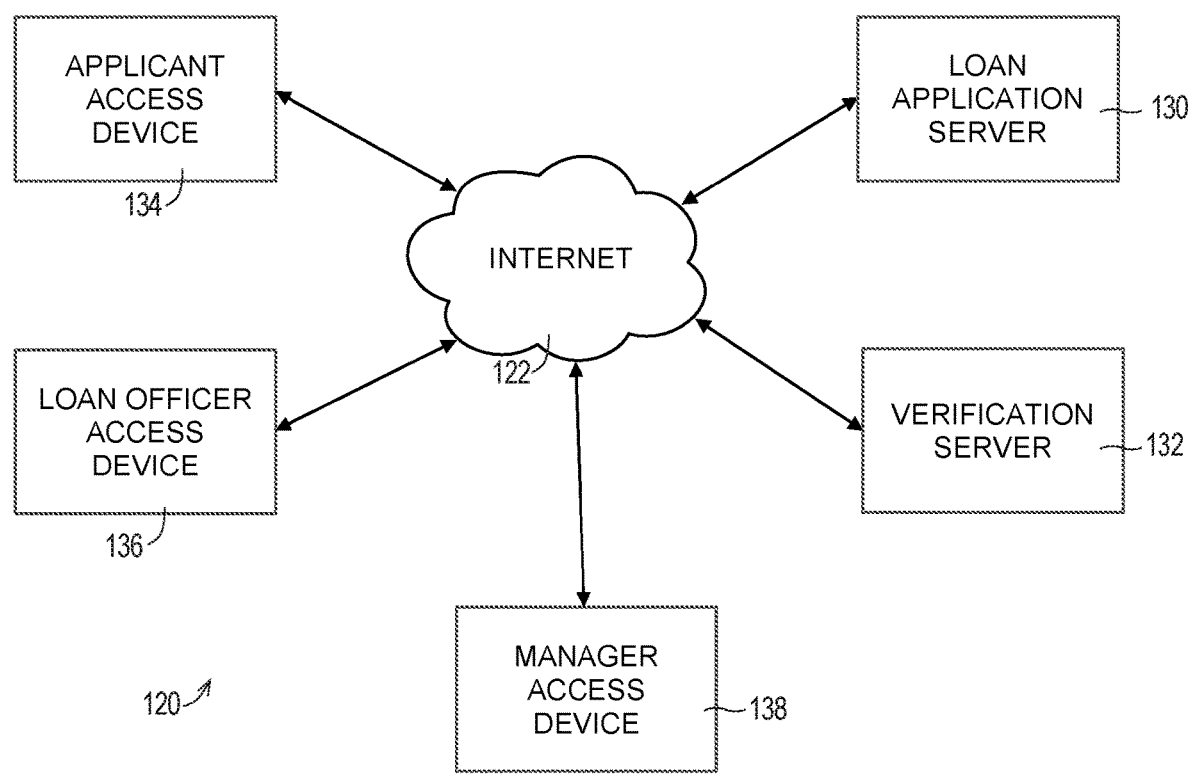
FIG. 9 is a block diagram illustrating a loan verification system of the present invention.

FIG. 9 illustrates a loan processing system 120 employing the verification systems and methods of the present invention. The example loan processing system 120 incorporates a communications system 122 such as the Internet and comprises a loan application server 130, a verification server 132, an applicant access device 134, a loan officer access device 136, and a manager access device 138.

In the example loan processing system 120, the loan application server 130 is a combination of computer hardware and software forming an online service capable of storing and allowing access to the data required to process loan applications and generating reports based on such data. The example verification server 132 is a combination of hardware and software capable of storing data and performing a compare operation as will be described below. The example applicant access device 134 is a tablet such as an iPad, while the loan officer access device 136 and manager access device 138 are smart phones such as an iPhone. However, a typical user may have multiple access devices, and different access devices may be used at different points in the process described herein.

As an alternative to using access devices 134, 136, and 138 separate from the verification server 132, the functions of the verification server 132 may be performed on any one or all of the access devices 134, 136, and 138. As another alternative, more than one verification server 132 may be provided.

While verification server 132 and access devices 134, 136, and 138 are depicted separately in FIG. 9, these verification services and access services may be performed on a single piece of hardware. For example, the manager access device 138 may contain software forming the verification server 132.

Figure 10:
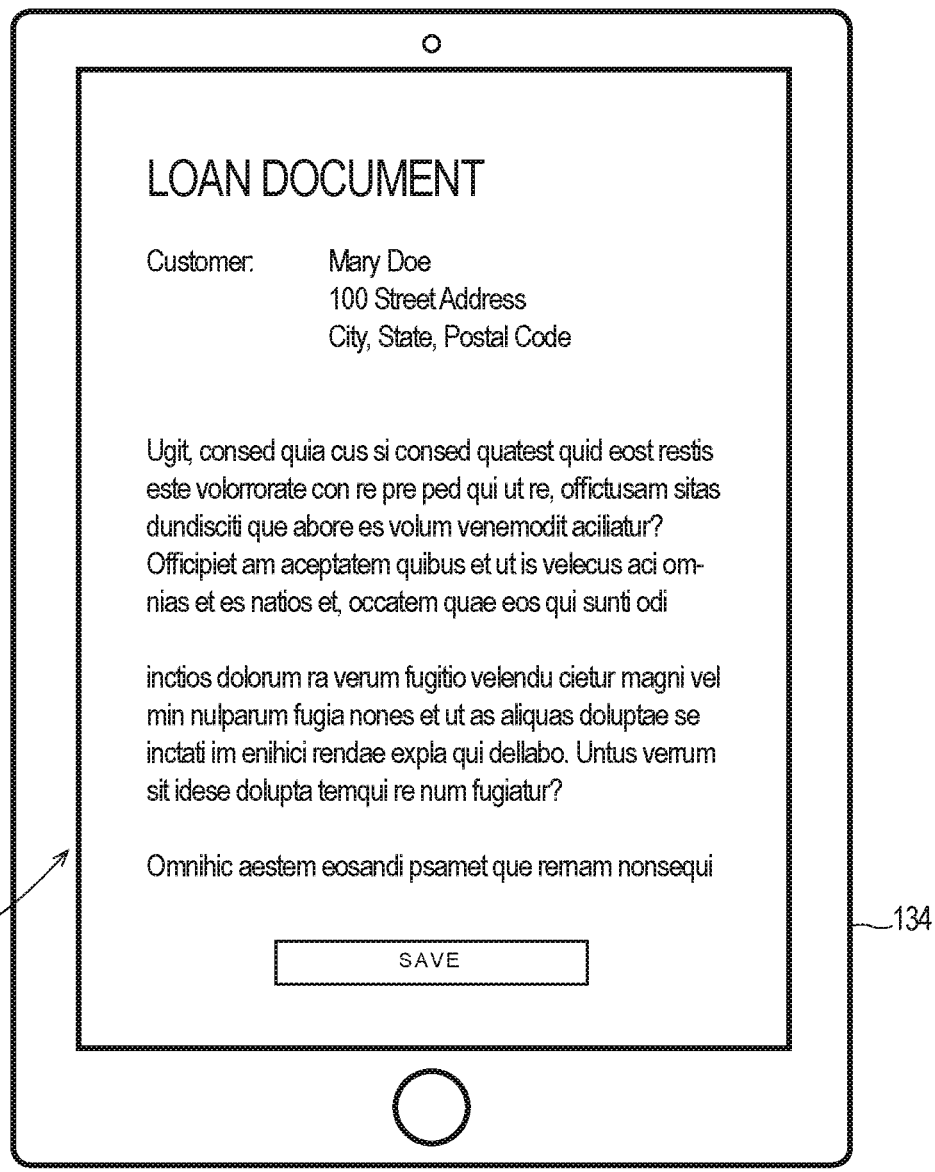
FIG. 10 is a screen shot of a display generated by an applicant access device during the loan processing example of the present invention, the display displaying a digital loan document.

Initially, a customer meets with a loan officer to finalize details of a loan application. As shown in FIG. 10, the loan application may be represented as a loan document 140 displayed on the applicant access device 134. The loan application server 130 will also maintain user accounts associated with the applicant operating the applicant access device 134, the loan officer operating the loan officer access device 136, and the manager operating the manager access device 138. The loan document 140 will also be associated with user accounts. The loan document 140 represents controlled data stored by the loan application server 130, and each such loan document will be associated with a unit set of user accounts.

The verification server 132 will maintain user accounts associated with the applicant operating the applicant access device 134, the loan officer operating the loan officer access device 136, and the manager operating the manager access device 138. The user accounts stored by the verification server 132 will further contain a reference signature created by each user.

Figure 11:
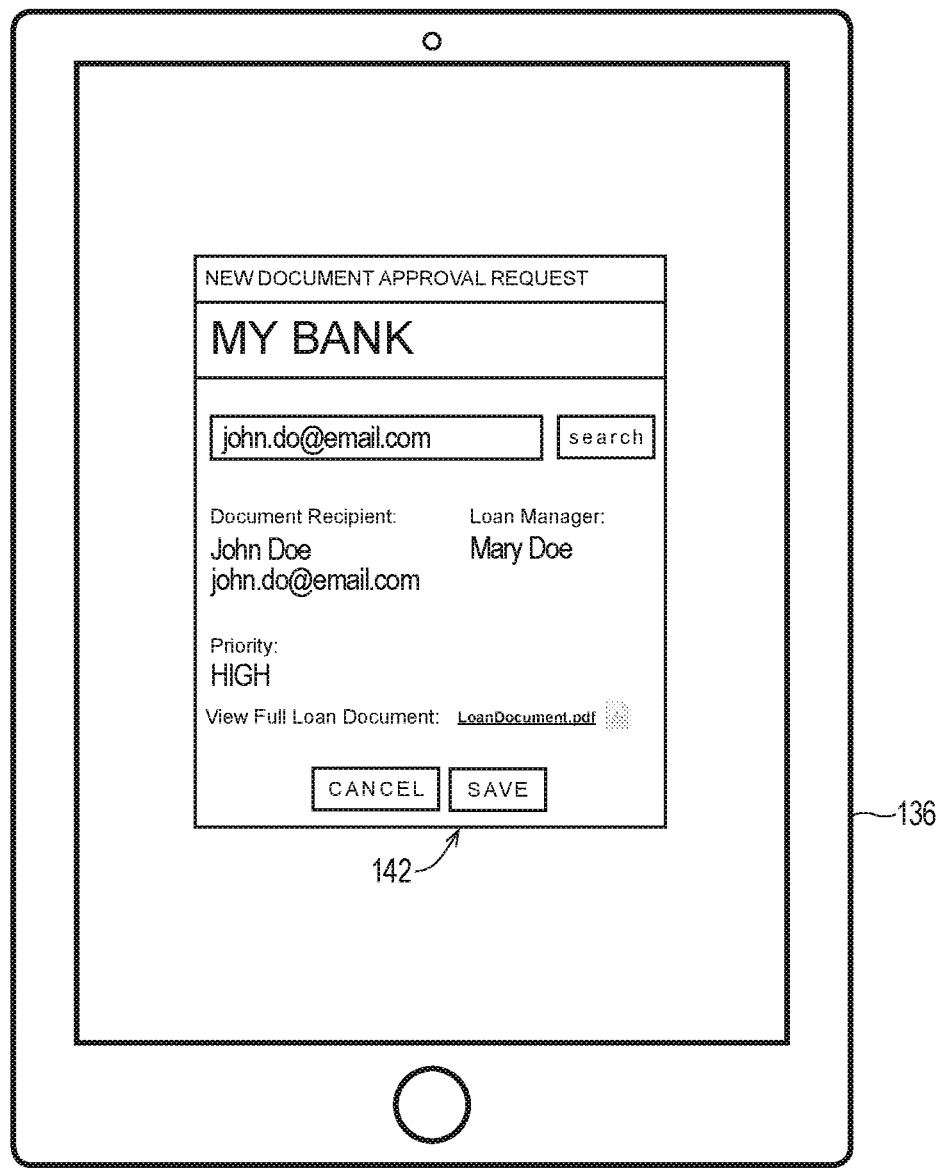
FIG. 11 is a screen shot of a display generated by a loan officer access device during a loan processing example of the present invention, the display displaying a document approval request form.
Figure 12:
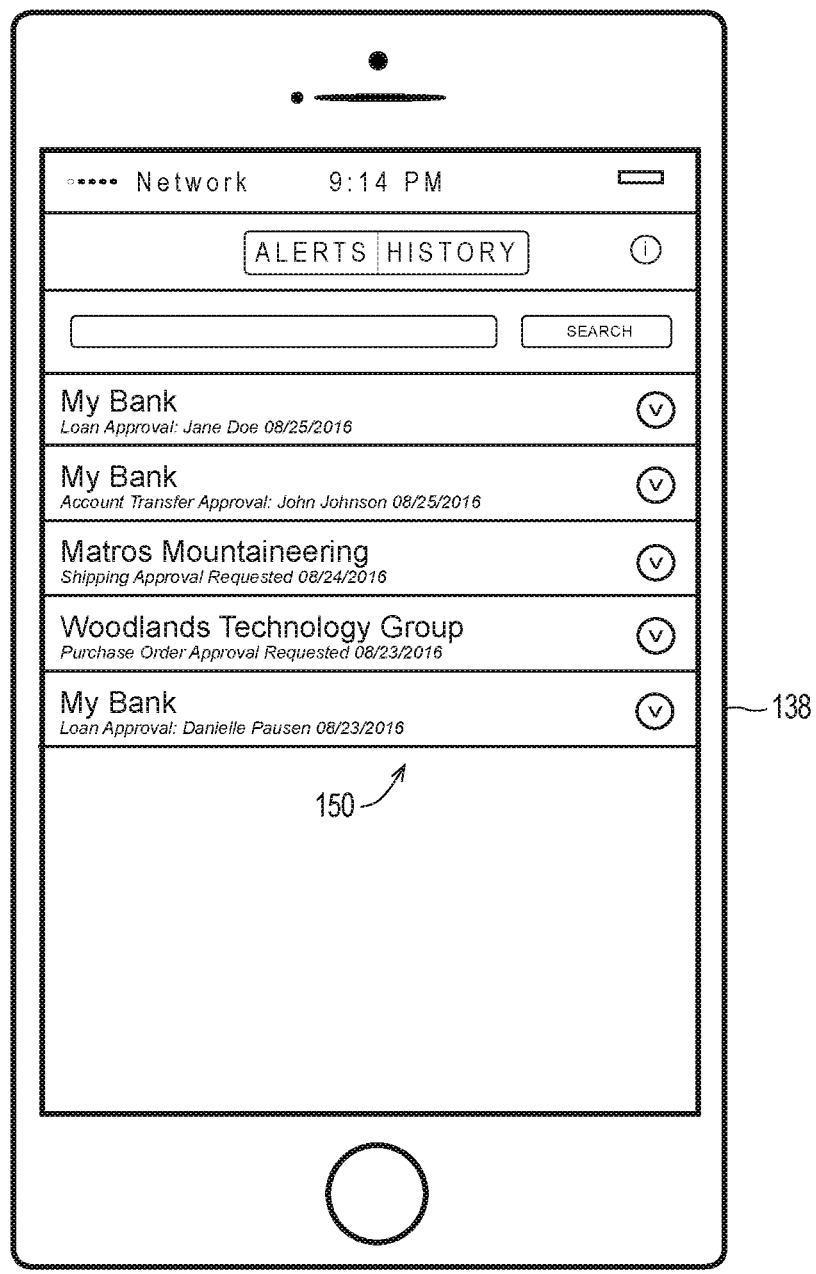
FIG. 12 is a screen shot of a display generated by a manager access device during the loan processing example of the present invention, the display displaying a list of alerts associated with a particular loan manager.

Next as shown in FIG. 11, a loan officer uses the loan officer access device 136 to submit a loan approval request 142 so that the loan manager can review and approve the loan. As shown in FIG. 12, the loan manager receives an alert on the manager access device 138 indicating, among other action items, that the loan application is awaiting review. Alerts 150 are viewed in this example by comparing a session signature entered by the manager with a pre-approved reference signature stored in the verification server 132.

Figure 13:
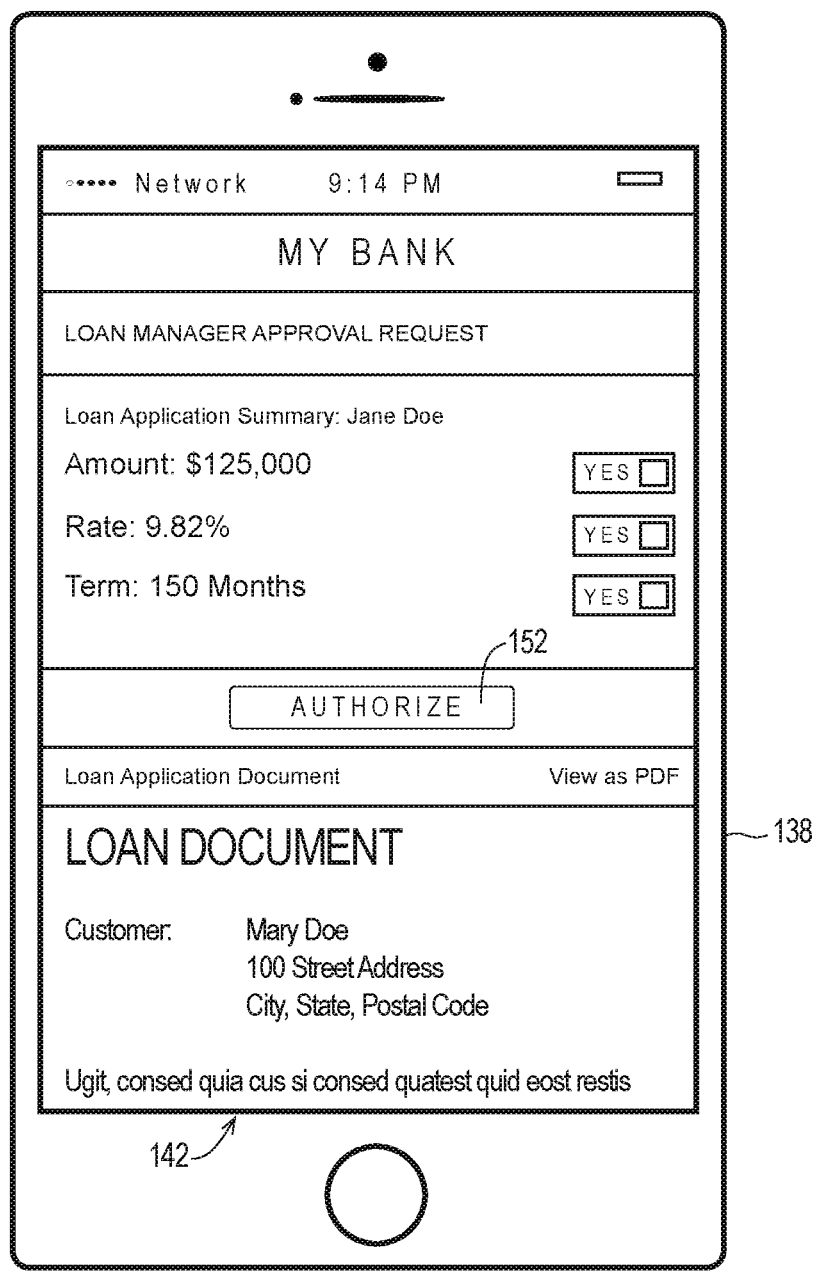
FIG. 13 is a screen shot of a display generated by the manager access device during the loan processing example of the present invention, the display displaying a selected loan application for approval.
Figure 14:
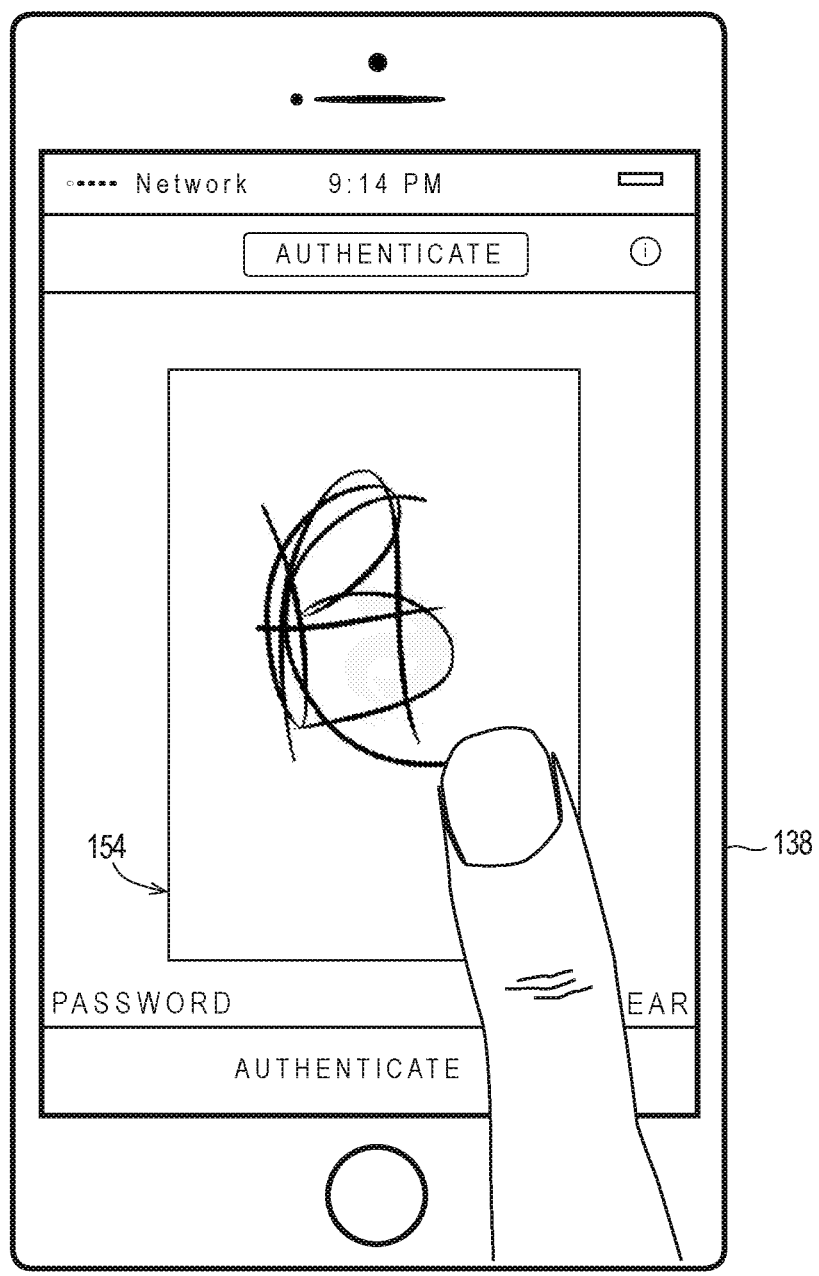
FIG. 14 is a screen shot of a display generated by the manager access device during the loan processing example of the present invention, the display displaying the process of interacting with the manager access device to enter an Asignio™ signature.

At this point, the loan manager, from the list of displayed alerts displayed on the manager access device 138 as depicted in FIG. 12, taps the alert associated with the loan application to be approved, authenticates using the verification server 132, and then reviews the loan application displayed on the manager access device as shown in FIG. 13. In particular, the loan manager taps the "AUTHORIZE" button 152 displayed in conjunction with the loan application displayed in FIG. 13 and authenticates using the verification process to record approval. FIG. 14 illustrates the process of entering the loan manager's session signature 154 on the manager access device 138; the manager access device 138 and the verification server 132 cooperate to compare the manager's session signature with the manager's reference signature and record authorization of the approval of the loan application if the two signatures are within predetermined parameters of each other.

Figure 15:
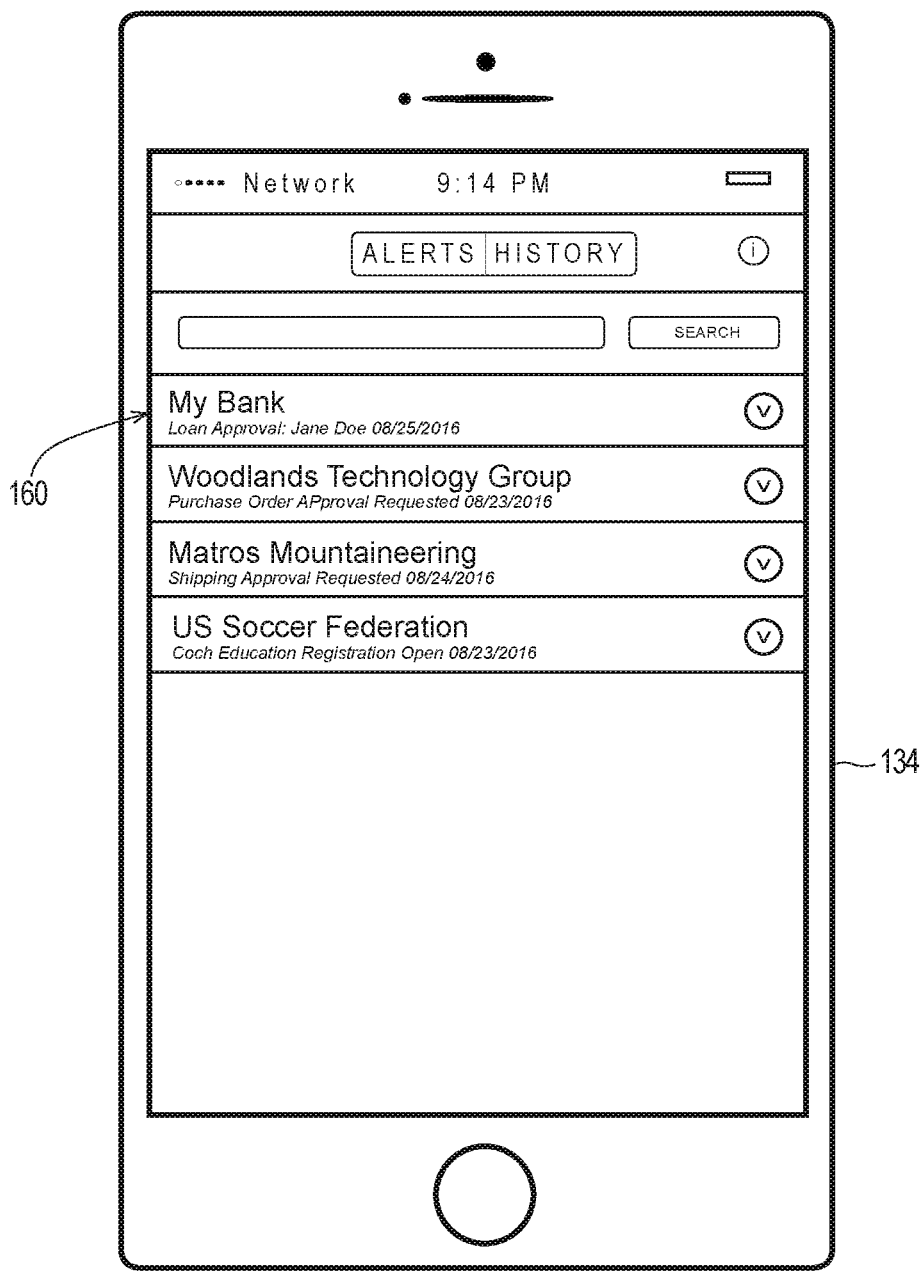
FIG. 15 is a screen shot of a display generated by the applicant access device during the loan processing example of the present invention, the display displaying a list of alerts associated with customer.

After the loan manager approves the loan application, the customer receives on the applicant access device 134 an alert 160 that the loan documents are now ready for final approval. FIG. 15 illustrates the process by which the user selects (e.g., taps on the applicant access device 134) the alert associated with the loan awaiting final approval. The loan document is displayed on the applicant access device 134 for final review and approval by the customer.

Figure 16:
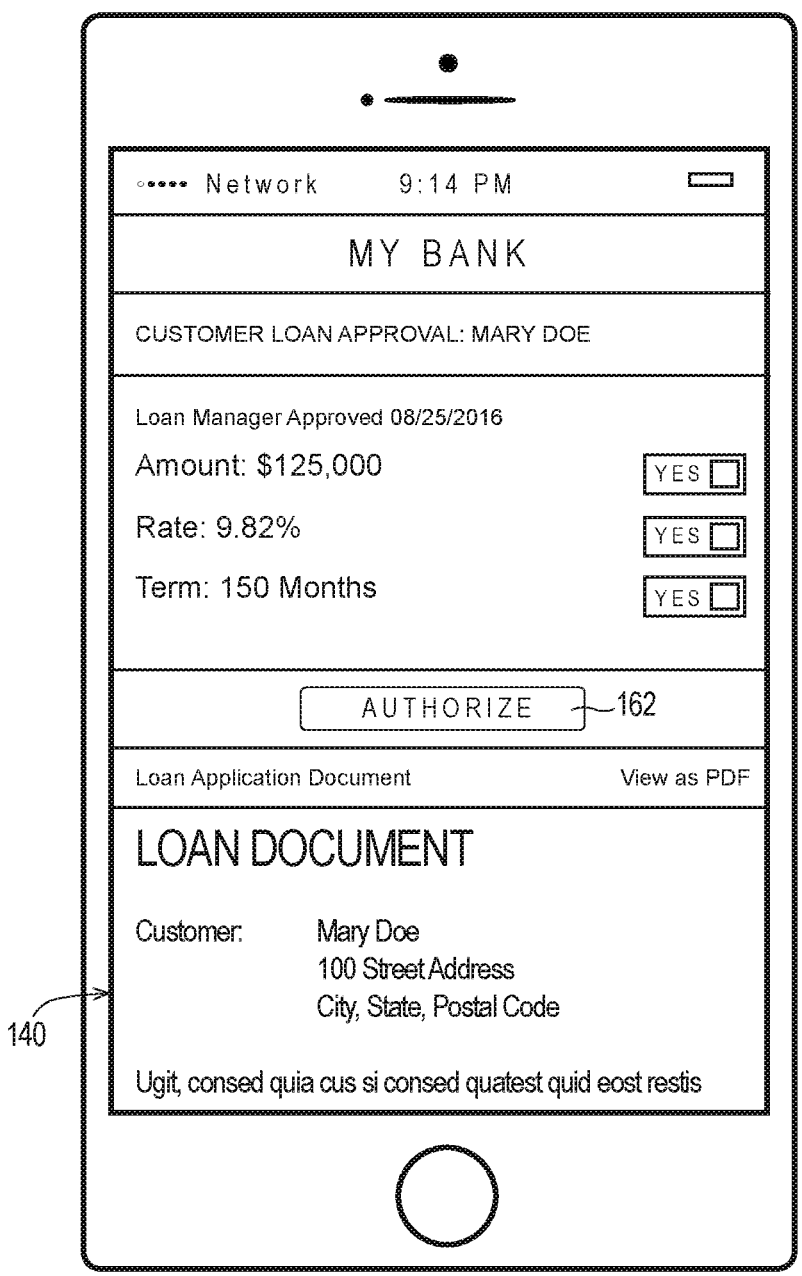
FIG. 16 is a screen shot of a display generated by the applicant access device during the loan processing example of the present invention, the display displaying a selected loan application for approval.
Figure 17:
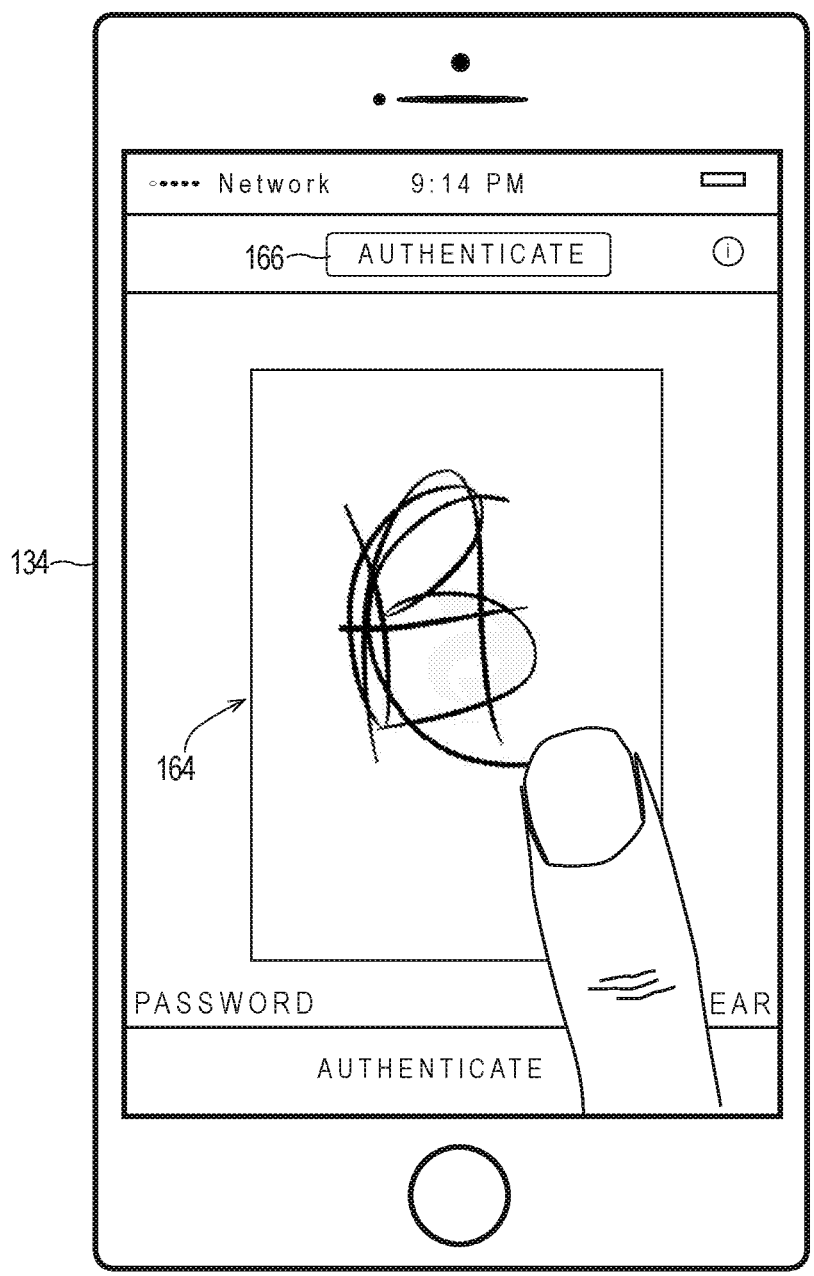
FIG. 17 is a screen shot of a display generated by the applicant access device during the loan processing example of the present invention, the display displaying the process of interacting with the applicant access device to enter an Asignio™ signature.

After reviewing the approved loan application, the customer taps the "AUTHORIZE" button 162 as shown in FIG. 16 to indicate approval of the terms of the loan. As shown in FIG. 17, after the applicant taps the "AUTHORIZE" button, the applicant authenticates by entering their session signature 164 and pressing the authenticate button 166 on the applicant access device 134 to record the approval. In particular, the approval is recorded only if the session signature substantially matches the pre-approved reference signature previously entered by the user in the verification server 132.

After the customer has recorded approval of the loan, the loan officer receives notification on the loan officer access device 136; the notification indicates that the loan application status has been changed to fully approved.

In the process described above, the manager first approved the loan application, and then the applicant approved the loan application in its final form. These two approvals need not be performed sequentially. The authentication systems and methods can instead be performed in parallel: the manager and the applicant are both simultaneously notified that the loan application is ready for approval, and the loan application status is changed to fully approved only after both the manager and the applicant have completed the approval process using the authentication systems and methods of the present invention.

III. Prescription Approval Example

Figure 18:
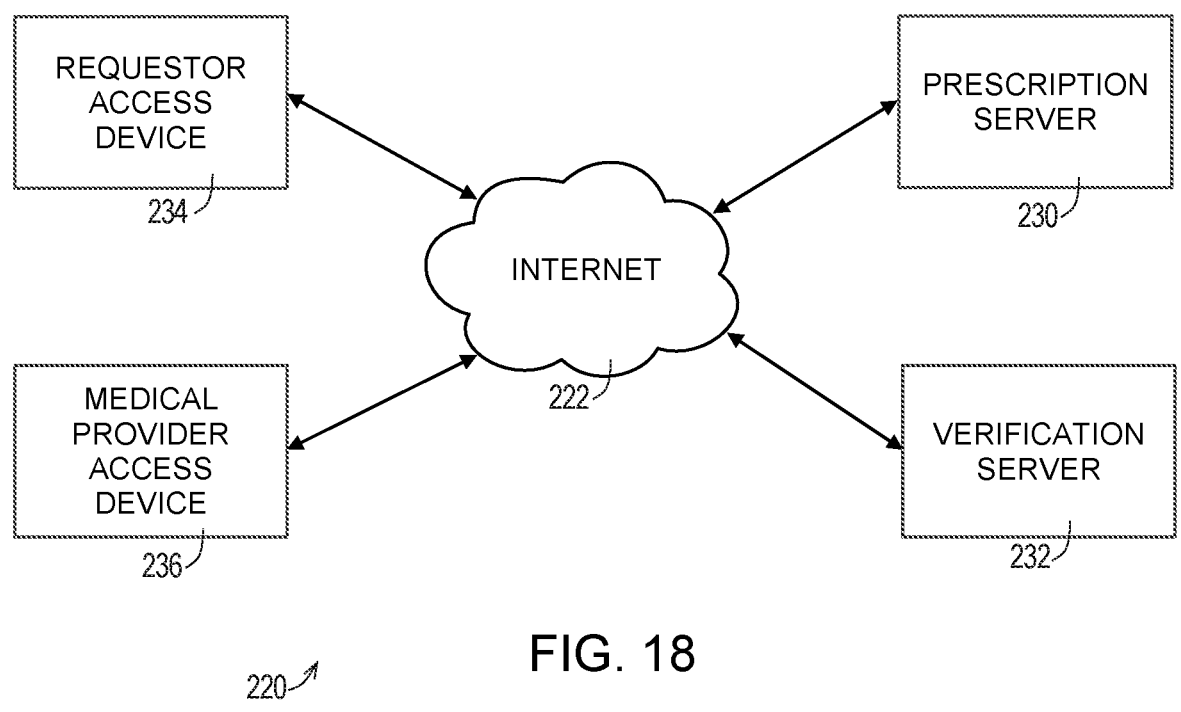
FIG. 18 is a block diagram illustrating a medical prescription approval system of the present invention.

Turning now to FIG. 18 of the drawing, depicted therein is a prescription approval system 220 constructed in accordance with, and embodying, the principles of the present invention. The example prescription approval system 220 incorporates a communications system 222 such as the Internet and comprises a prescription server 230, a verification server 232, a requestor access device 234, and a medical provider device 236.

In the example prescription approval system 220, the prescription server 230 is a combination of computer hardware and software forming an online service capable of storing and allowing access to the data required to process loan applications and generating reports based on such data. The example verification server 232 is a combination of hardware and software capable of storing data and performing a compare operation as will be described below. The example requestor access device 234 is a tablet such as an iPad, while the example medical provider device 236 is a smart phone such as an iPhone. However, a typical user may have multiple access devices, and different access devices may be used at different points in the process described herein.

As an alternative to using access devices 234 and 236 separate from the verification server 232, the functions of the verification server 232 may be performed on one or both of the access devices 234 and 236. As another alternative, more than one verification server 232 may be provided.

While verification server 232 and access devices 234 and 236 are depicted separately in FIG. 18, these verification services and access services may be performed on a single piece of hardware. For example, the medical provider access device 236 may contain software forming the verification server 232.

Figure 19:
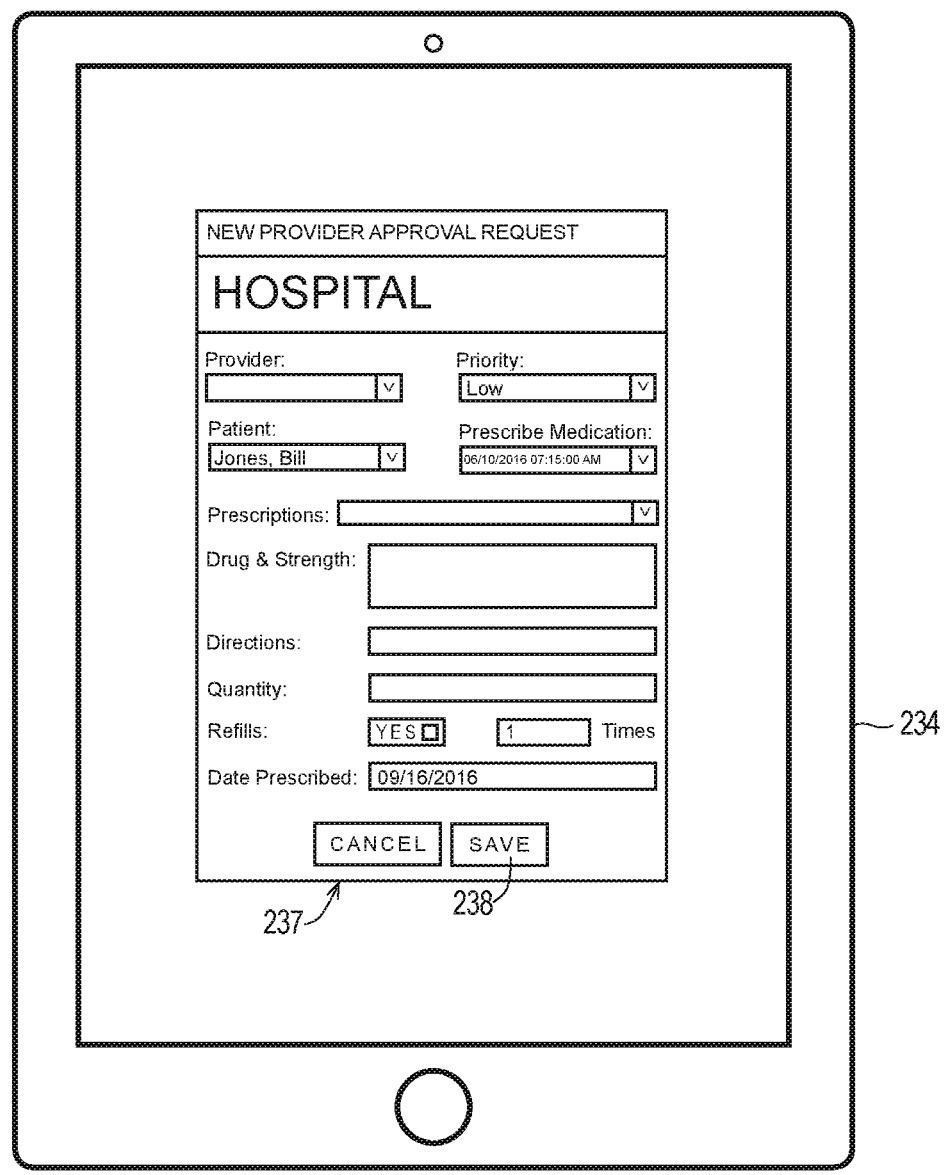
FIG. 19 is a screen shot of a display generated by a requestor access device during the prescription processing example of the present invention, the display displaying a digital prescription request form.

After a medical appointment, the requestor (e.g., nurse) reviews the necessary prescriptions and issues a prescription request 237 as shown in FIG. 19. The requestor presses a save button 238 to save the prescription request 237 using the requestor access device 234, and a notification is sent to the approving medical provider that approval of a prescription is requested.

Figure 20:
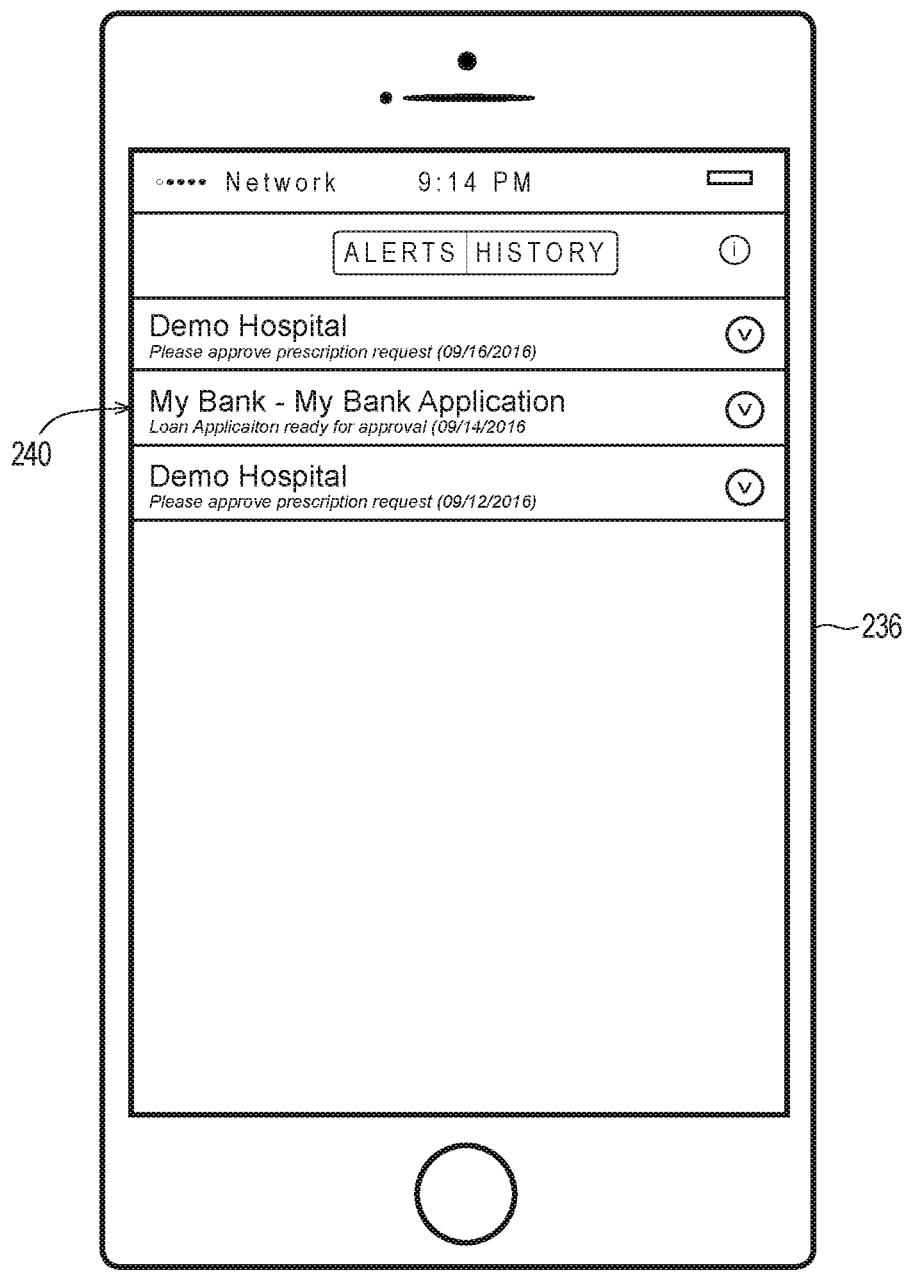
FIG. 20 is a screen shot of a display generated by medical provider access device during the prescription processing example of the present invention, the display displaying a list of alerts.
Figure 21:
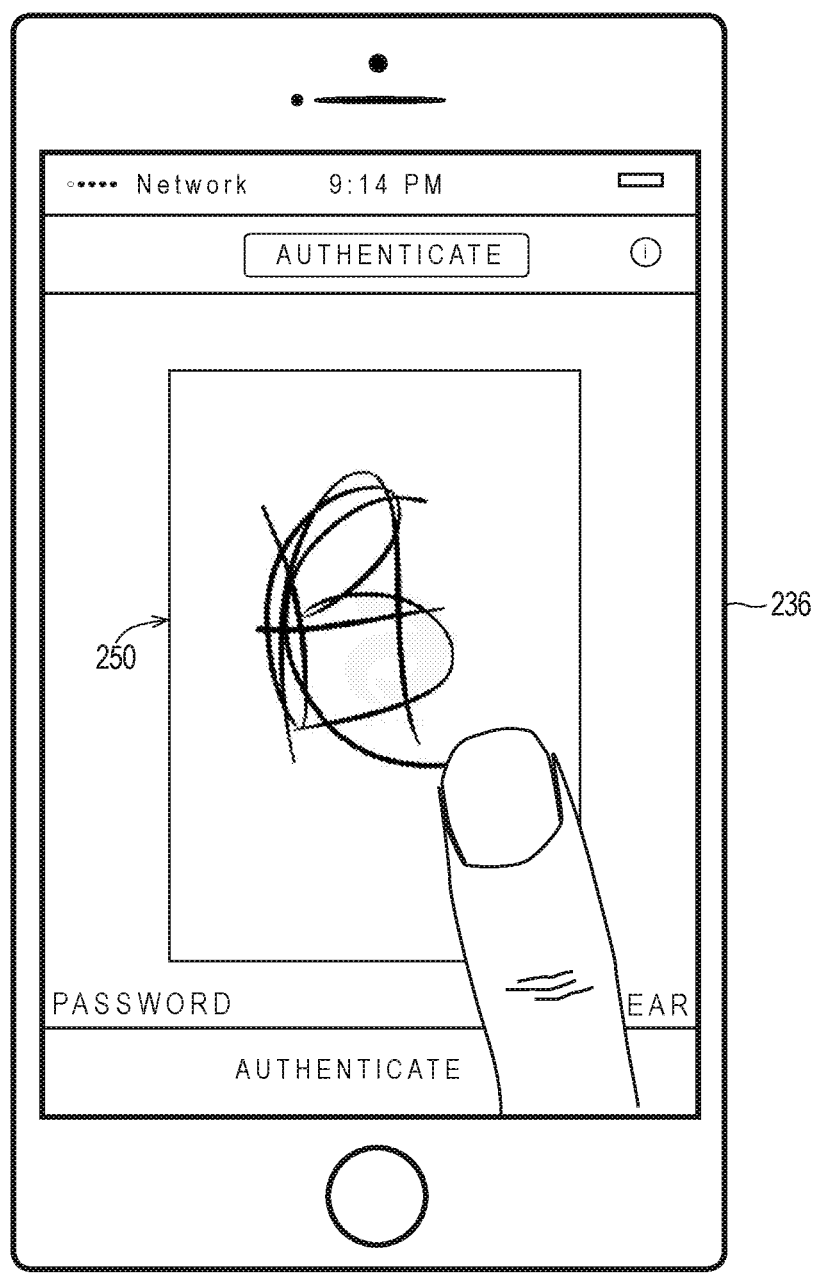
FIG. 21 is a screen shot of a display generated by a medical provider access device during the prescription processing example of the present invention, the display displaying the process of interacting with the medical provider access device to enter an Asignio™ signature.

FIG. 20 illustrates that the approving medical provider (e.g., doctor) receives an alert 240 on the medical provider access device 236 notifying the medical provider that a new prescription is awaiting approval. Alerts are viewed in this example by authenticating using a pre-approved signature as shown in FIG. 21. The approving medical provider taps the alert, authenticates with their pre-approved signature, and then reviews the prescription request.

Figure 22:
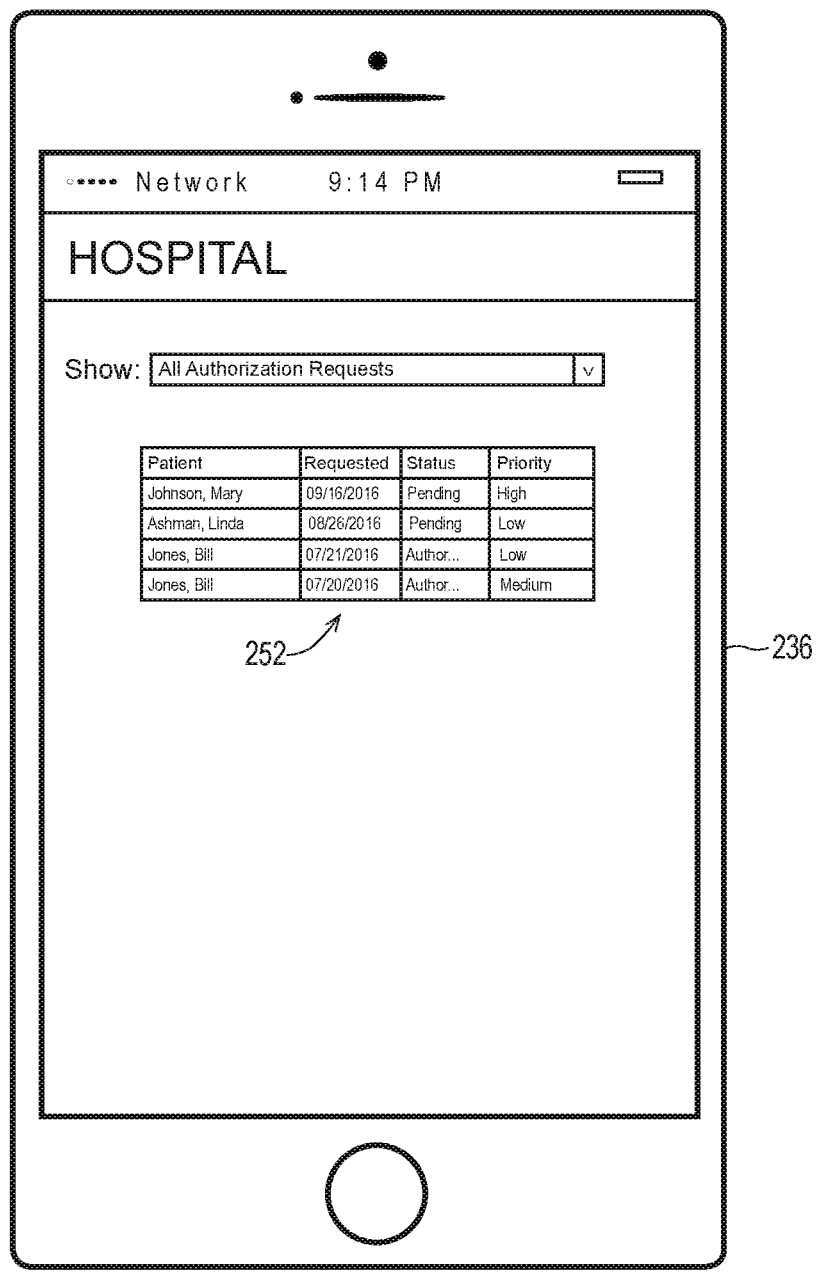
FIG. 22 is a screen shot of a display generated by a medical provider access device during the prescription processing example of the present invention, the display displaying a list of prescription requests awaiting approval.
Figure 23:
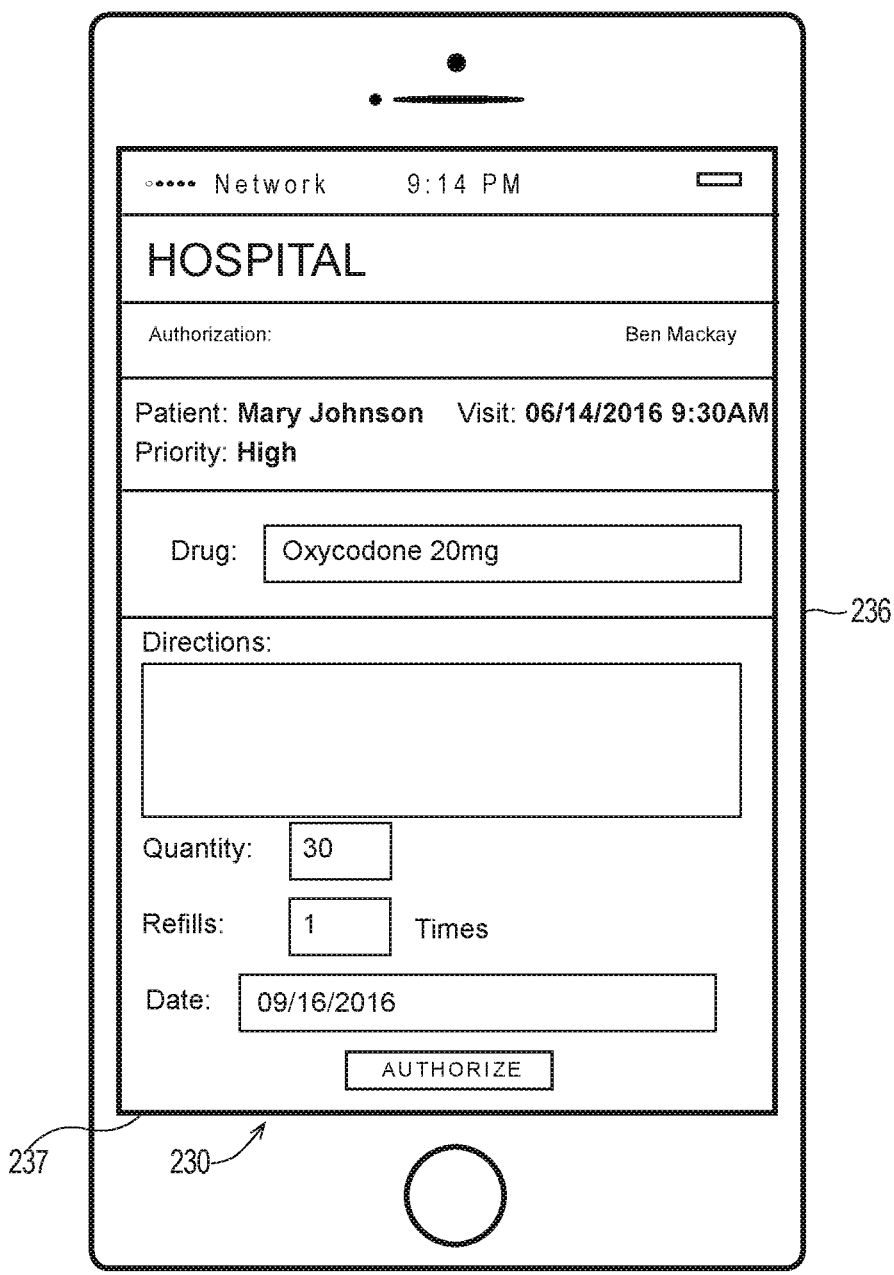
FIG. 23 is a screen shot of a display generated by a medical provider access device during the prescription processing example of the present invention, the display displaying the details of a selected prescription request awaiting approval.
Figure 24:
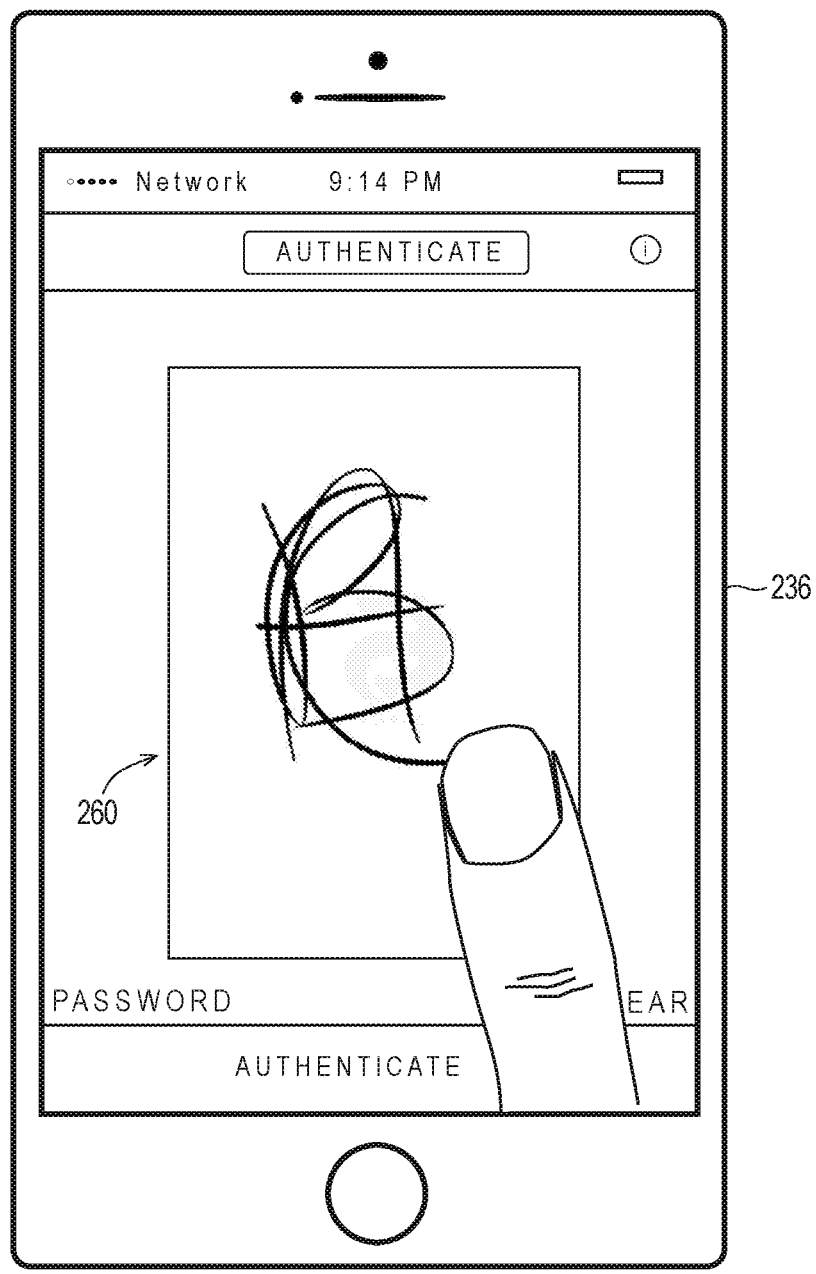
FIG. 24 is a screen shot of a display generated by a medical provider access device during the prescription processing example of the present invention, the display displaying the process of interacting with the medical access device to enter an Asignio™ signature.

In particular, after authenticating by entering a signature at 250 to view the details of the alert, a list 252 of prescriptions awaiting approval is displayed for viewing by the medical provider on the medical provider access device 236 as shown in FIG. 22. And as shown in FIG. 23, tapping on a displayed prescription request causes information associated with the selected prescription request 237 to be displayed on the medical provider access device 236 for review and approval by the medical provider. After the medical provider taps the alert, the example system 220 requests additional authentication to approve the prescription on the medical provider device as shown at 260 in FIG. 24. The medical provider may edit the selected prescription request if necessary.

Figure 25:
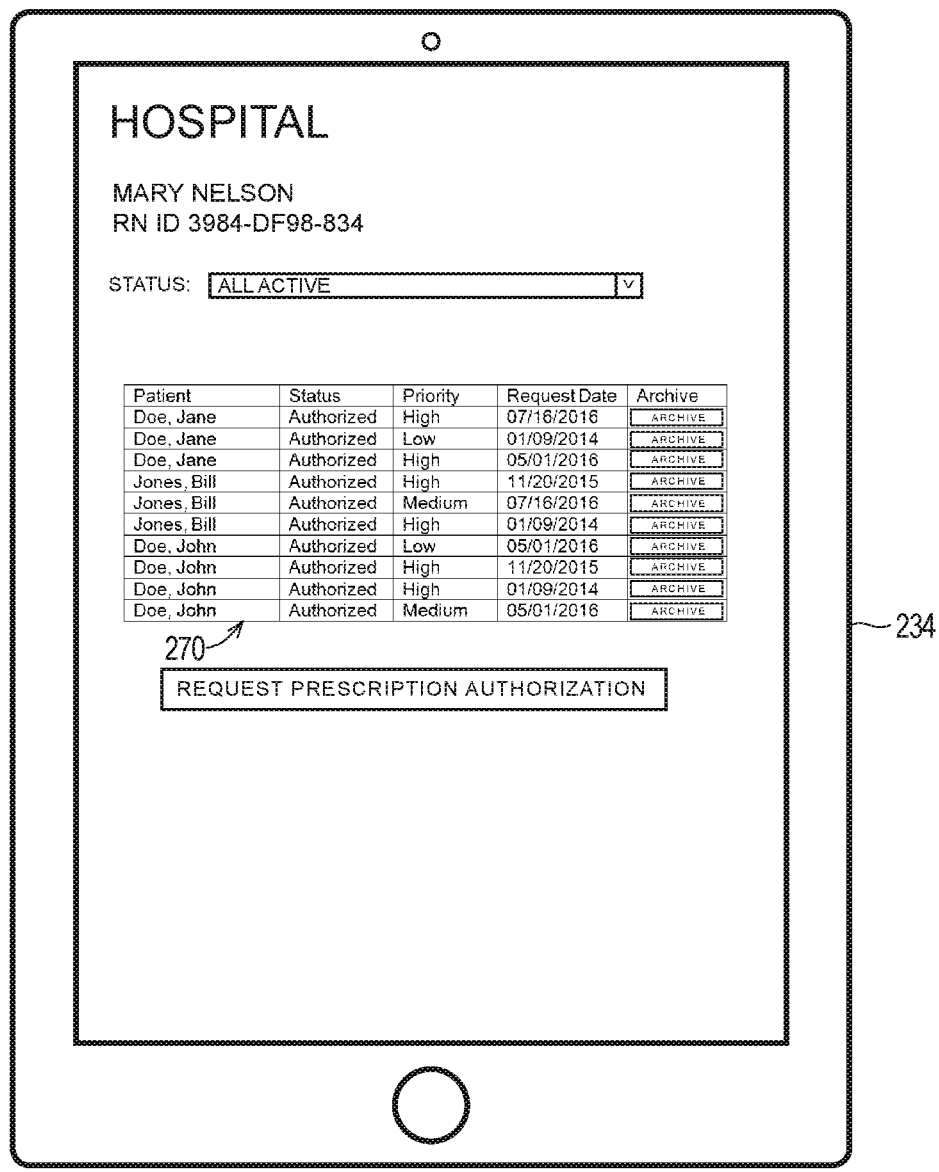
FIG. 25 is a screen shot of a display generated by the requestor access device during the prescription processing example of the present invention, the display displaying a list of requested prescriptions and also the authorization status of each requested prescription.

FIG. 25 illustrates that the nurse/requestor receives notification in a list 270 on the requestor access device 234 that the medical provider has approved the prescription, and the requestor can take appropriate action.

IV. Authentication Systems and Methods

Figure 26:
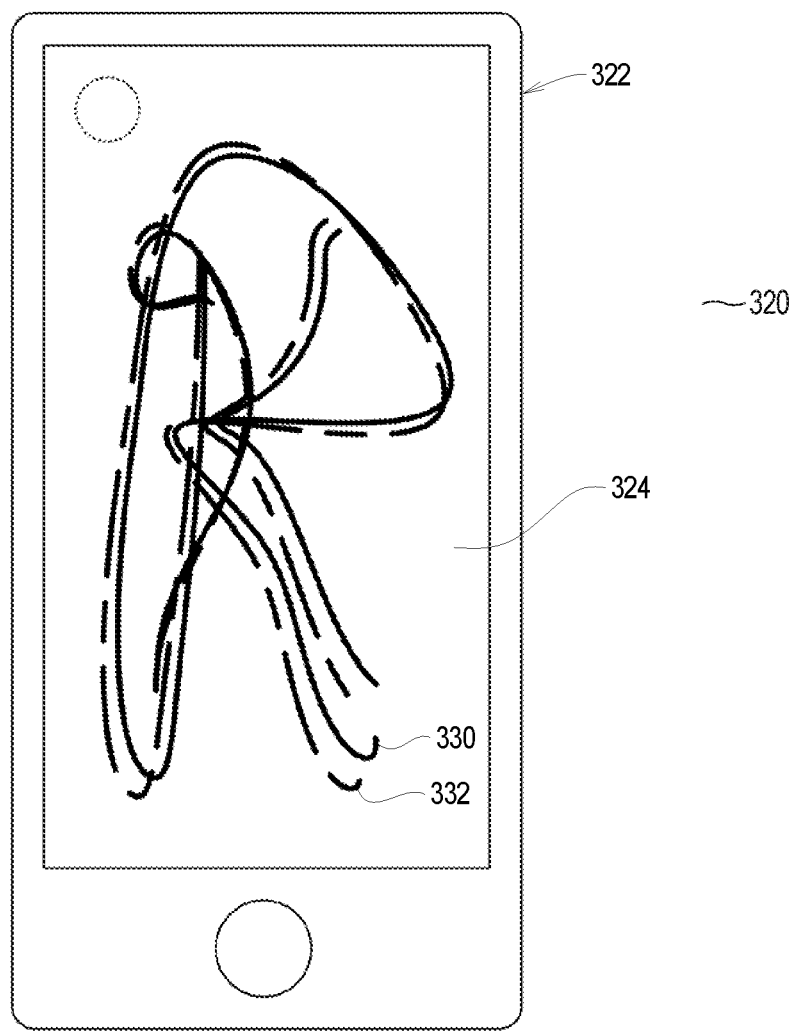
FIG. 26 illustrates the entry of a signature into a customer mobile device using a touch screen thereof as part of the step of validating a transaction.
Figure 27:
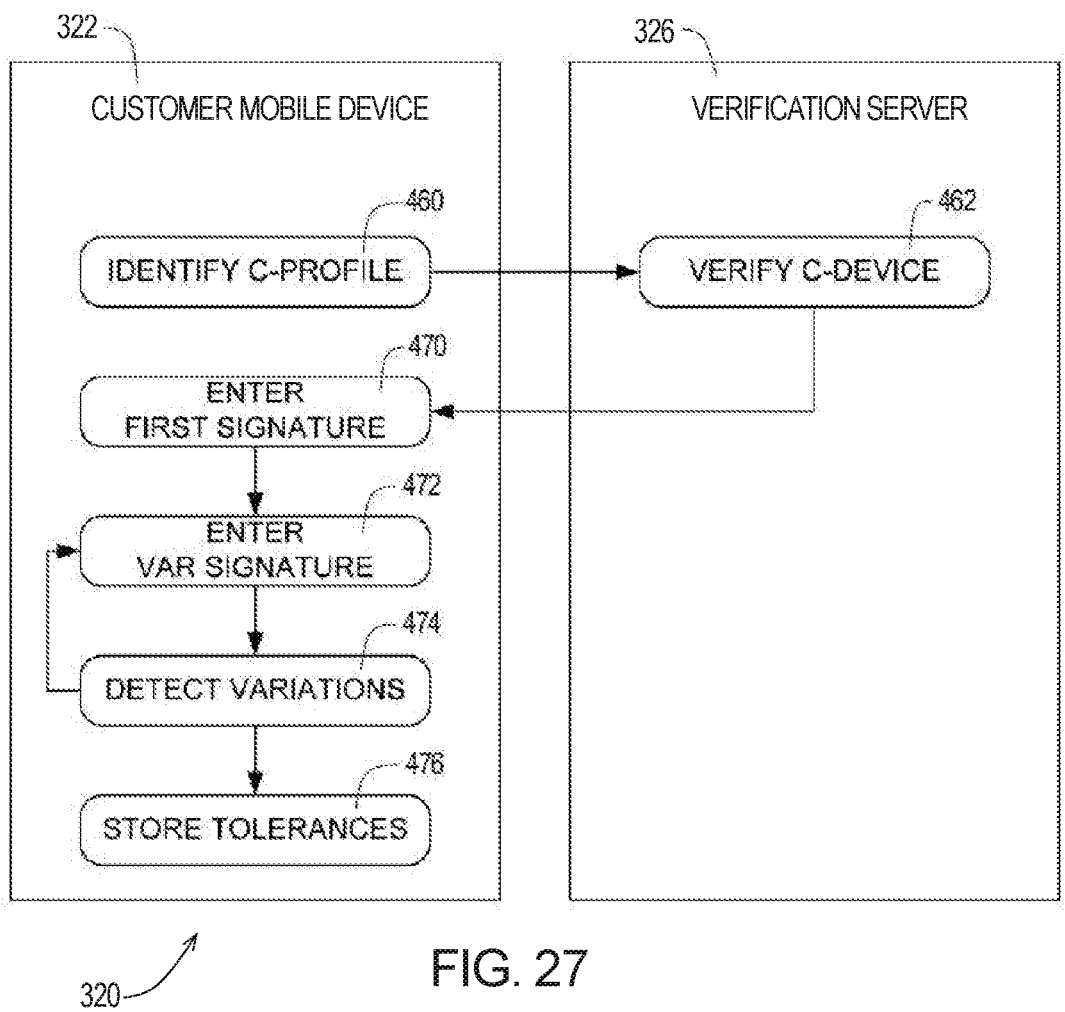
FIG. 27 is a flow chart illustrating the step of verifying the customer's signature when performing the step of validating a transaction as described above with respect to FIG. 1 or as used as part of the example loan processing system of FIG. 9 and the prescription processing system of FIG. 18.

Turning now to FIGS. 26-28, an example authentication system 320 that may be used with any of the example systems 20, 120, and 220 to authenticate whether an entered signature matches a reference signature associated with a particular user. Examples of the use of authentication systems similar to the example authentication system 320 described herein are described in the Applicant's Co-Pending U.S. patent application Ser. No. 14/501,554. The '554 application is incorporated herein by reference to the extent that the teachings of the '554 application illustrate examples of alternative authentication systems that may be used in place of the example authentication system 320 described herein.

The process of entering a signature for authentication purposes is shown, for example, in FIG. 26. FIG. 26 illustrates that the example verification system 320 comprises a mobile device 322 comprising a display 324 that allows a user to enter a shape using a finger, stylus, or the like. In the example verification system 320, the example mobile device 322 is used in conjunction with a verification server 326 as shown in FIG. 27.

Referring initially to FIG. 26, it can be seen that a handwritten entered signature depicted by solid lines 330 is entered on the mobile device 322, and a pre-approved reference signature is indicated by broken lines at 332. The reference signature 332 is depicted in FIG. 26 for illustrative purposes only and would, in fact, not be displayed on the device 322.

The handwritten signature 330, which also may be referred to as a session signature, will be displayed as formed by the individual authorizing the transaction using the mobile device 322. The handwritten signature 330 will be compared in software with the reference signature 332, and the handwritten signature 330 will be verified only when it deviates no more than a predetermined amount from the reference signature 332. As can be seen in FIG. 26, the handwritten signature 330 substantially matches the reference signature 332 and would likely be verified. It should be noted that the concept of "deviation" incorporates more than spatial or shape deviation. When the reference signature is generated, characteristics such as timing, speed, pressure, and the like may also be measured. Acceptable deviations in these additional characteristics may also be considered when determining whether the handwritten signature 330 substantially matches the reference signature 332 and is verified.

FIGS. 27 and 28A-28D illustrate the process of preparing the mobile device 322 to authenticate the identity of the user by creating a reference signature such as the reference signature 332 described above. The process depicted in FIG. 27 assumes that the mobile device 322 is loaded with an appropriate application and that the user has set up an appropriate profile. To create the reference signature 332, the user first uses the mobile device 322 to identify the appropriate profile at a step 460. The verification server 326 verifies the profile at step 462.

Figure 28A:
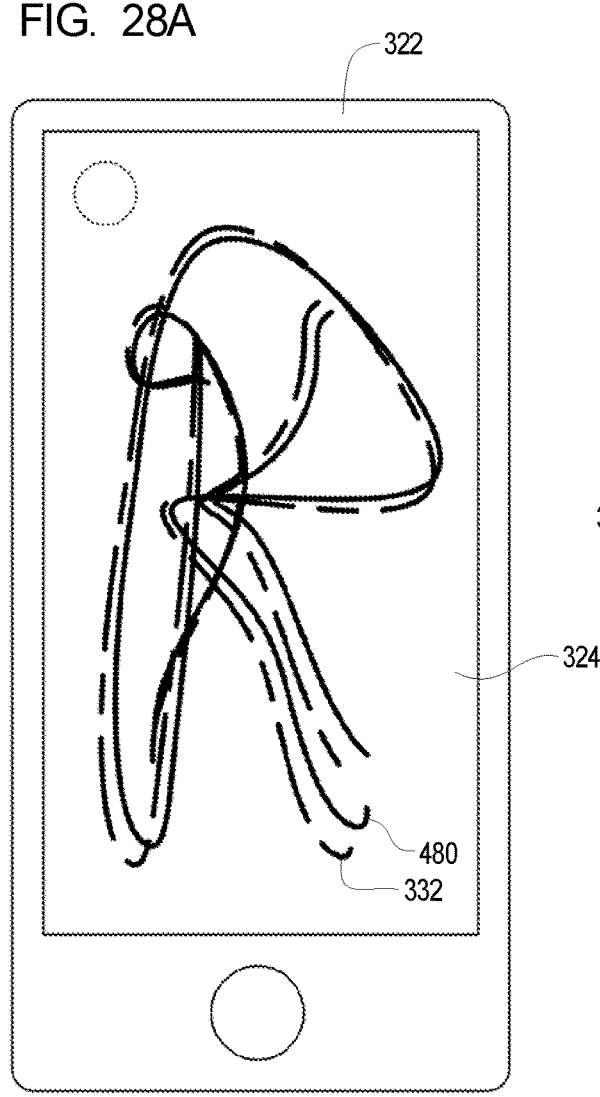
FIGS. 28A-28D illustrate the process of establishing a reference signature for use in the example validation step depicted in FIG. 27.

At a step 470, the user enters a first (calibration) signature using the mobile device 322 as generally described above. FIG. 28A shows both the first signature as represented by solid lines 480 and also represents the reference signature 332 using dotted lines. Again, the dotted lines are not actually displayed by the mobile device 322 but are depicted in FIG. 28A to provide a reference point to illustrate the ultimate creation of the reference signature 332. The customer mobile device data associated with the first signature 480 is stored by the mobile device 322.

Figure 28B:

At a step 472, the user enters a second (calibration) signature using the mobile device 322. FIG. 28B shows both the second signature as represented by solid lines 482 and also represents the reference signature 332 using dotted lines. Again, the dotted lines are not actually displayed by the mobile device 322 but are depicted in FIG. 28B to provide a reference point to illustrate the ultimate creation of the reference signature 332. The customer mobile device data associated with the second signature 482 is stored by the mobile device 322. Variations between the first and second signatures 480 and 482 are used to generate a first iteration of the reference signature 332 at a step 474.

Figure 28C:
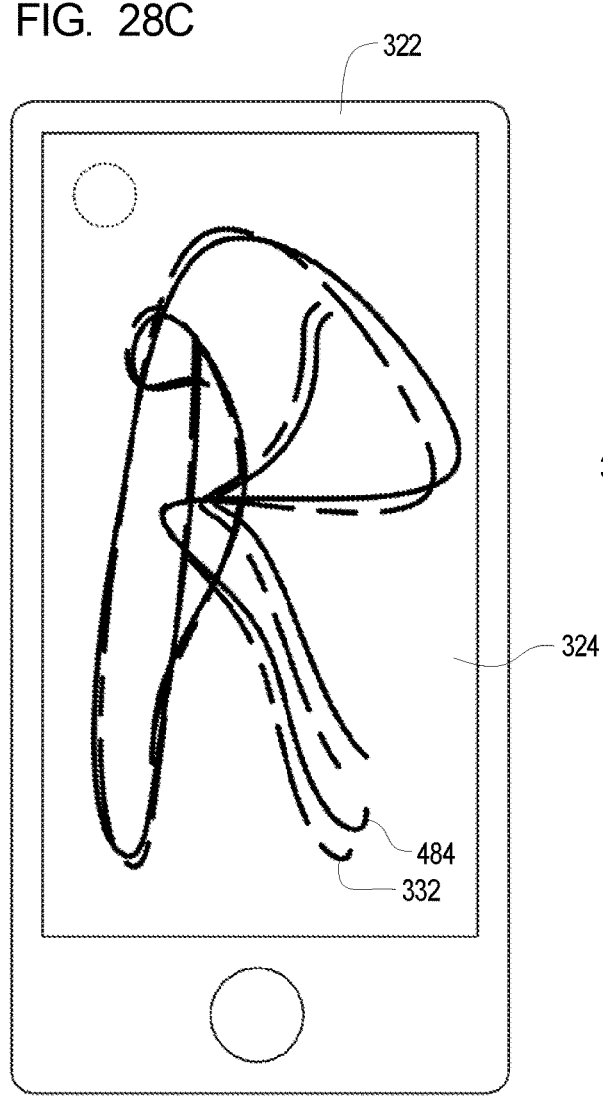

The process then returns to step 472, at which point the user enters a third (calibration) signature using the mobile device 322. FIG. 28C shows both the third signature as represented by solid lines 484 and also represents the reference signature 332 using dotted lines. Again, the dotted lines are not actually displayed by the mobile device 322 but are depicted in FIG. 28C to provide a reference point to illustrate the ultimate creation of the reference signature 332. The customer mobile device data associated with the third signature 484 is stored by the mobile device 322. Variations between the first, second, and third signatures 480, 482, and 484 are used to generate a first iteration of the reference signature 332 at the step 474.

Figure 28D:
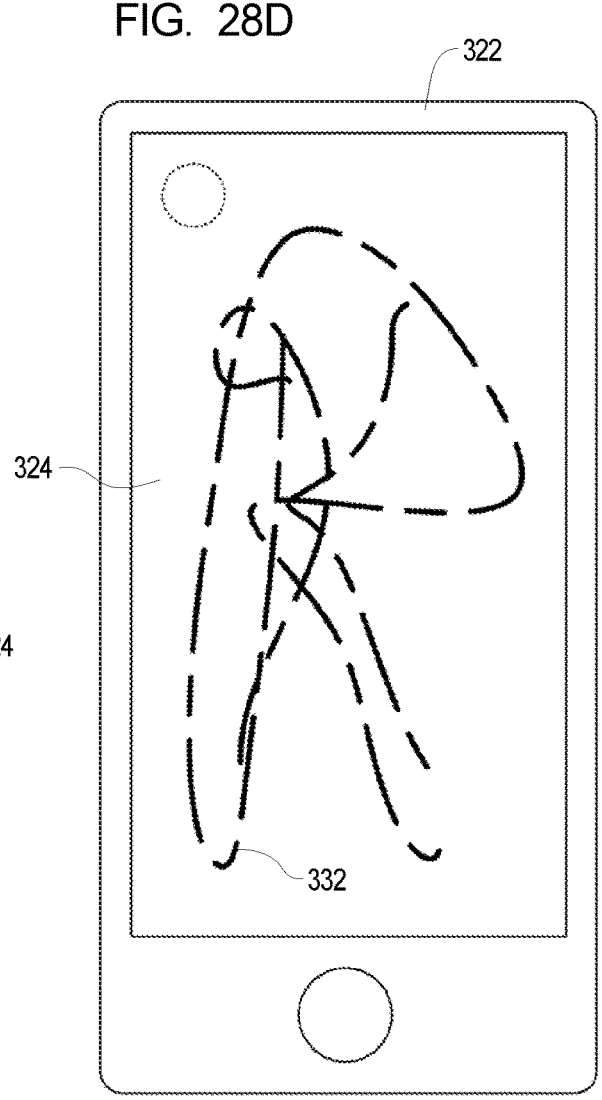

After enough signature entries to create a reference signature representative of tolerances among all of the various signatures 480, 482, and 484, plus any additional signatures entered as may be necessary to reduce the likelihood of error during the validation process, the reference signature 332 may be represented by a reference signature as shown by FIG. 28D, and FIG. 27 shows that acceptable variances from the reference signature are stored as tolerances at step 476. The reference signature 332 in conjunction with the variations as stored at step 476 thus incorporates variation data indicative of normal variations of actual signatures from the reference signature that are acceptable when determining whether a particular signature is valid.

V. Additional Considerations

The authentication systems and methods of the present invention may thus be used to log in to a device without a touch screen by entering a signature on a companion device having a touch screen. Authentication systems and methods of the present invention may also be used to approve of an electronic transaction such as a purchase, a loan application, or a prescription. And both of these uses may be combined: a user may perform most of the tasks of logging in and/or approving on a device without a touch screen, and then finalize or approve the transaction using a device with a touch screen.

What is claimed is:

1. An authentication system for allowing access to a user account server, comprising:
    a plurality of access devices capable of operatively connecting to the user account server, where at least one of the plurality of access devices comprises a touch screen for allowing entry of a plurality of calibration signatures and at least one session signature; and
    at least one verification server capable of comparing session signatures to reference signatures; wherein
    at least one user enters a plurality of calibration signatures using the touch screen of at least one of the plurality of access devices;
    a user reference signature is generated from the plurality of the calibration signatures, where the user reference signature includes spatial characteristics, and includes tolerances indicative of variations associated with spatial characteristics, and is stored on the at least one verification server;
    at least one user operates a first access device of the plurality of access devices to generate a verification image on the first access device;
    the at least one user operates a second access device of the plurality of access devices to generate a session ID by performing image analysis of the verification image, and send the session ID to the at least one verification server;
    when prompted by the at least one verification server, the at least one user operates the second access device to enter a user session signature;
    the second access device transmits the user session signature to the at least one verification server;
    after receipt of the session ID and the user session signature, the at least one verification server compares the user session signature with the user reference signature; and
    the at least one verification server selectively allows the at least one user to connect to the user account server using the first access device based on the comparison of the user session signature with the user reference signature.

2. An authentication system as recited in claim 1, in which the at least one verification server allows the at least one user to connect to the user account server using the first access device if the user session signature substantially matches the user reference signature.

3. An authentication system as recited in claim 1, in which:
    the second access device comprises:
        a touch screen for allowing entry of session signatures, and
        a sensor for generating scans; wherein the user interacts with the user account server using the first access device to request
            verification through the at least one verification server;
    the at least one verification server causes the first access device to generate the verification image;
    the user uses the second access device to generate a scan of the verification image; and based on the scan of the verification image, the at least one verification server communicates with the second access device to prompt the user to enter the user session signature on the second access device.

4. An authentication system as recited in claim 1, in which the at least one verification server allows the user to connect to the user account server using the first access device when the user session signature matches the user reference signature within the tolerances of the user reference signature.

5. An authentication system as recited in claim 1, in which:
the user account server stores controlled data; and
the user account server allows access by the at least one user to the controlled data based on the comparison of the user session signature with the user reference signature and the tolerances of the user reference signature.

6. An authentication system as recited in claim 1, in which:
the user account server stores controlled data; and
the user account server allows access by a plurality of users to the controlled data based on the comparison of a plurality of user session signatures with a plurality of user reference signatures and the tolerances forming a part of the plurality of user reference signatures.

7. An authentication system as recited in claim 6, in which:
the controlled data is associated with a loan application; and
the plurality of users comprises an applicant, a loan account officer, and a manager.

8. An authentication system as recited in claim 6, in which:
the controlled data is associated with a prescription; and
the plurality of users comprises a prescription requestor and a medical provider.

9. An authentication system as recited in claim 1, in which:
the user account server stores controlled data; and
the user account server allows access by first and second users to the controlled data based on the comparison of first and second user session signatures with first and second user reference signatures, respectively.

10. A method of allowing access to a user account server, comprising:
operatively connecting at least one of a plurality of access devices to the user account server, where at least one of the at least one access device comprises a touch screen for allowing entry of signatures; and
providing at least one verification server capable of comparing session signatures to reference signatures;
entering a plurality of calibration signatures using at least one access device;
establishing, based on variations among the plurality of calibration signatures, a user reference signature, where the user reference signature includes spatial characteristics, and tolerances indicative of variations associated with spatial characteristics;
storing the user reference signature on the at least one verification server;
operating a first access device of the plurality of access devices to generate a verification image on the first access device;
operating a second access device of the plurality of access devices to generate a session ID by performing image analysis of the verification image, and send the session ID to the at least one verification server;
when prompted by the at least one verification server, operating the second access device to enter a user session signature;
causing the second access device to transmit the user session signature to the at least one verification server; and
after receipt of the session ID and the user session signature, operating the at least one verification server to compare the user session signature with the user reference signature; and
operating the at least one verification server selectively to allow the at least one user to connect to the user account server using the first access device based on the comparison of the user session signature with the user reference signature.

11. A method as recited in claim 10, in which the at least one verification server allows the at least one user to connect to the user account server using the first access device if the user session signature substantially matches the user reference signature.

12. A method as recited in claim 10, in which:
the user account server stores controlled data; and
the user account server allows access by the at least one user to the controlled data based on the comparison of the user session signature with the user reference signature and the tolerances of the user reference signature.

13. A method as recited in claim 10, in which:
the user account server stores controlled data; and
the user account server allows access by a plurality of users to the controlled data based on the comparison of a plurality of user session signatures with a plurality of user reference signatures and the tolerances of the plurality of user reference signatures.

14. A method as recited in claim 13, in which:
the controlled data is associated with a loan application; and
the plurality of users comprises an applicant, a loan account officer, and a manager.

15. A method as recited in claim 13, in which:
the controlled data is associated with a prescription; and
the plurality of users comprises a prescription requestor and a medical provider.

16. An authentication system for allowing access to a controlled data stored on a user account server, comprising:
a plurality of access devices capable of operatively connecting to the user account server, where at least one of the plurality of access devices comprises a touch screen for allowing entry of signatures; and
at least one verification server capable of comparing session signatures to reference signatures;
wherein at least one user enters a plurality of calibration signatures using the touch screen of at least one of the plurality of access devices;
a user reference signature is generated from the plurality of calibration signatures, where the user reference signature
includes spatial characteristics,
includes tolerances indicative of variations associated with spatial characteristics, and
is stored on the at least one verification server;
at least one user operates a first access device of the plurality of access devices to generate a verification image on the first access device;
the at least one user operates a second access device to generate a session ID by performing image analysis of the verification image, and send the session ID to the at least one verification server;

when prompted by the at least one verification server, the at least one user operates the second access device to enter a user session signature before the verification server allows access to the user account server;

the second access device transmits the user session signature to the at least one verification server;

after receipt of the session ID and the user session signature, the at least one verification server compares the user session signature with the user reference signature; and the at least one verification server selectively allows the at least one user to connect to the user account server using the first access device based on the comparison of the user session signature with the user reference signature.

17. An authentication system as recited in claim 16, in which:

the user interacts with the user account server using the first access device to request verification through the at least one verification server;

the at least one verification server causes the first access device to generate the verification image;

the user uses the second access device to generate a scan of the verification image;

based on the scan of the verification image, the at least one verification server communicates with the second access device to prompt the user to enter the user session signature on the second access device; and the at least one verification server allows the user to access the controlled data on the user account server using the first access device based on a comparison of the user session signature with the user reference signature.

18. An authentication system as recited in claim 1, in which the user account server allows access by a plurality of users to the controlled data based on the comparison of a plurality of user session signatures with a plurality of user reference signatures.

19. An authentication system as recited in claim 18, in which:

the controlled data is associated with a loan application; and the plurality of users comprises an applicant, a loan account officer, and a manager.

20. An authentication system as recited in claim 18, in which:

the controlled data is associated with a prescription; and the plurality of users comprises a prescription requestor and a medical provider.

\* \* \* \* \*